US008507519B2

(12) United States Patent
Patel et al.

(10) Patent No.: US 8,507,519 B2
(45) Date of Patent: *Aug. 13, 2013

(54) ANTIBACTERIAL OPTICALLY PURE BENZOQUINOLIZINE CARBOXYLIC ACIDS, PROCESSES, COMPOSITIONS AND METHODS OF TREATMENT

(75) Inventors: Mahesh Vithalbhai Patel, Aurangabad (IN); Shivkumar Agarwal, Aurangabad (IN); Sreenivas Kandepu, Guntur (IN)

(73) Assignee: Wockhardt Limited, Mumbai (IN)

( * ) Notice: Subject to any disclaimer, the term of this patent is extended or adjusted under 35 U.S.C. 154(b) by 1009 days.

This patent is subject to a terminal disclaimer.

(21) Appl. No.: 11/804,770

(22) Filed: May 21, 2007

(65) Prior Publication Data

US 2008/0044466 A1 Feb. 21, 2008

Related U.S. Application Data

(63) Continuation of application No. 09/566,875, filed on May 8, 2000, now Pat. No. 7,247,642.

(60) Provisional application No. 60/170,676, filed on Dec. 14, 1999.

(30) Foreign Application Priority Data

May 7, 1999 (WO) .................. PCT/IN99/00016

(51) Int. Cl.
*A61K 31/4375* (2006.01)
*C07D 487/12* (2006.01)

(52) U.S. Cl.
USPC ..................... 514/294; 514/233.2; 546/94

(58) Field of Classification Search
None
See application file for complete search history.

(56) References Cited

U.S. PATENT DOCUMENTS

| | | | |
|---|---|---|---|
| 3,924,042 A | 12/1975 | Gerster ................ | 424/258 |
| 3,984,403 A | 10/1976 | Fujisawa | |
| 3,985,882 A | 10/1976 | Gerster ................ | 424/258 |
| 4,007,266 A * | 2/1977 | Choay .................. | 424/582 |
| 4,051,247 A | 9/1977 | Schuppan et al. ...... | 424/258 |
| 4,364,929 A * | 12/1982 | Sasmor et al. ......... | 424/78.07 |
| 4,399,134 A | 8/1983 | Ishikawa et al. ....... | 424/246 |
| 4,404,207 A | 9/1983 | Stern .................. | 424/258 |
| 4,416,884 A | 11/1983 | Ishikawa et al. ....... | 424/250 |
| 4,443,447 A | 4/1984 | Gerster et al. ......... | 424/248 |
| 4,472,406 A | 9/1984 | Gerster ................ | 424/258 |
| 4,472,407 A | 9/1984 | Stern .................. | 424/258 |
| 4,535,161 A | 8/1985 | Hayakawa ............ | 546/94 |
| 4,552,879 A | 11/1985 | Ishikawa et al. ....... | 514/253 |
| 4,594,347 A | 6/1986 | Ishikawa et al. ....... | 514/252 |
| 4,599,418 A | 7/1986 | Irikura et al. .......... | 544/361 |
| 4,642,355 A | 2/1987 | Nakamura | |
| 4,740,374 A * | 4/1988 | Nakano et al. ......... | 424/448 |
| 5,185,337 A | 2/1993 | Fujii et al. ............ | 514/254 |
| 5,424,290 A * | 6/1995 | Maloy et al. ........... | 514/13 |
| 5,795,909 A * | 8/1998 | Shashoua et al. ....... | 514/449 |
| 5,859,026 A | 1/1999 | Ito et al. .............. | 514/312 |
| 5,889,009 A | 3/1999 | Miyake et al. .......... | 514/254 |
| 6,034,100 A | 3/2000 | Adachi et al. .......... | 514/312 |
| 6,121,285 A | 9/2000 | Takemura et al. ....... | 514/312 |
| 6,184,388 B1 | 2/2001 | Takemura et al. ....... | 548/566 |
| 6,329,391 B1 | 12/2001 | Ledoussal et al. ...... | 514/312 |
| 6,608,078 B2 | 8/2003 | De Souza et al. | |
| 6,750,224 B1 | 6/2004 | Patel et al. | |
| 6,753,333 B2 | 6/2004 | De Souza et al. | |
| 7,164,023 B2 | 1/2007 | Deshpande et al. | |
| 2004/0176321 A1 | 9/2004 | Saoji et al. | |
| 2004/0176337 A1 | 9/2004 | Saoji et al. | |
| 2005/0054666 A1 | 3/2005 | Deshpande et al. | |
| 2007/0167627 A1 | 7/2007 | Deshpande et al. | |
| 2008/0044466 A1 | 2/2008 | Patel et al. | |
| 2008/0108646 A1* | 5/2008 | Patel et al. ............ | 514/294 |

OTHER PUBLICATIONS

Takahasi. Arzneimittelforschung. Feb. 1995;45(2):195-7. Links.*
Kido. Chem Pharm. Bull 42(4)872-876 (1994).*
Swarbrick & Boylan. Encyclopedia of Pharmaceutical Technology vol. 13. Copyright 1996.*
Hashimoto. Chem Pharm. Bull 44(4):642-645 (1996).*
Takahasi. Arzneimittelforschung. Feb. 1995;45(2):195-7.*
Morita. Tetrahedron:Asymmetry 6(1):245-254 (1995).*
Eichenfield. Pediatrician. 1991;18(3):218-23.*
Kido. Chem. Pharm. Bull 42(4) 872-876 (1994).*
Kurokawa. J Am Acad Dermatol. Oct. 1991;25(4):674-81.*
Pfau. J Urol. Mar. 1993;149(3):532-4.*
Puschett. Cardiology. 1994;84 Suppl 2:4-13.*
Hopkins. Drugs and Pharmacology for Nurses 13th Edition. Copyright 1999.*
Hashimoto, K., et al. "A Practical Synthesis of (S)-(−)-Nadifloxacin: Novel Acid-Catalyzed Racemization.." Chem. Pharm. Bull. vol. 44, No. 4 (1996) pp. 642-645.
Irish, D. et al. Control of an Outbreak of an Epidemic Methicillin-Resistant *Straphylococcus aureus* also Resistant to Mupirocin, Journal of Hospital Infection vol. 39 (1998(pp. 19-26 (XP-000884368).
Kido, M. et al. Crystal Structures of Nadifloxacin Anhydride and Its Hemihydrate. Chem. Pharm Bull. vol. 42 No. 4 (1994) pp. 872-876.
Kido, M. et al. "The Absolute Configuration of (R)-(+)Nadfloxacin" Chem.Pharm. Bull. vol. 44 No. 2 (1996) pp. 421-423.
Miller, M.A., et al. Development of Mupirocin Resistance Among Methicillin-Resistant *Staphylococcus aureus* . . . Infection Control and Hospital Epidemiology vol. 17, No. 12 (1995) pp. 811-813 (XP-000884374).
Nishjima, S., et al. "Sensitiivty of *Staphylococcus aureus*, Isolated from Skin Infections in 1994, to 19 Antimicrobial Agents" The Journal of Int'l Medical Research vol. 23 (1995) pp. 328-334 (XP000884323).

(Continued)

*Primary Examiner* — David J Blanchard
*Assistant Examiner* — Lori K Mattison
(74) *Attorney, Agent, or Firm* — Ladas & Parry LLP

(57) ABSTRACT

The present invention relates to optically pure S-(−)-benzoquinolizine carboxylic acid, lysine salt and to pharmaceutical compositions comprising the S(−)-benzoquinolizine carboxylic acid, lysine salt.

5 Claims, 10 Drawing Sheets

(56) References Cited

OTHER PUBLICATIONS

Nishijima, S. et al. "Activity of Eight Fluoroquinolones Against Both Methicillin-Susceptible and Resistant *Staphylococcus aureus* . . . "Journal of Dermatology vol. 22 (1995) pp. 153-155 (XP-000884341).
Nishijima, S., et al. "Activity of Nadifloxacin Against Methicillin-Resistant *Staphylococcus aureus* Isolated from . . . " The Journal of Int'l Medical Research vol. 24 (1996) pp. 12-16 (XP-000884325).
Oizumi, N. et al. "Relationship between mutations in the DNA gyrase and topoisomerase IV genes and nadifloxacin . . . *Staphylococcus aureus*" J. Infect Chemotherapy, vol. 7, p. 191-194, (2001).
Haustein, U-F., et al. "Topical quinolone nadifloxacin (OPC-7251) in bacterial skin disease: clinic evaluation . . . testing" J. of Dermatological Treatment, vol. 8, p. 87-92, (1997).
Ishikawa, et al. Chem Pharm. Bull. (1989) 37 (8) pp. 2103-2108.
Abstract: Koike, M. et al. "Metabolic Fate of (.+−.)-9-fluoro-6,7,dihydro-8-(4-hydroxy-1-piperidyl) Rabbits and Dogs" Iyakuhin Kenkyu vol. 21, No. 5 (1990) pp. 998-1021.
Abstract: Koike, M. et al. "Metabolic Fate of (.+−.)-9-fluoro-6,7,dihydro-8-(4-hydroxy-1-piperidyl) Rabbits and Dogs" Iyakuhin Kenkyu vol. 21, No. 5 (1990) pp. 1022-1033.
Abstract: Fujita, S. et al. :General Pharmacology of ((.+−.)-9-fluoro-6,7,dihydro-8-(4-hydroxy-1-piperidyl) . . . antibacterial agent lyakuhin Kenkyu vol. 21, No. 6 (1990) pp. 1156-1176.
Abstract: Yasuo, A. et al. "Pharmacokinetics and Safety Evaluation of OPC-7251 Cream After Topical . . . Volunteers" Yakuri to Chiryo vol. 18, No. 4 (1990) pp. 1717-1730.
Abstract:: Asada, Y. et al. "Pharmacokinetics and Toxicity of OPC-7251 Cream After Topical Applications . . . Volunteers"Yakuri to Chiryo vol. 18, No. 4 (1990) pp. 1717-1730.
Abstract: Awogi, et al. "Genotoxicity Studies of (.+−.)-9-fluoro-6,7,dihydro-8-(4-hydroxy-1-piperidyl) . . . Antibacterial Agent" lyakuhin Kenkyu vol. 21, No. 4 (1990) pp. 626-635.
Abstract: Matsuzawa, A. et al. "Reproductive and Developmental Toxicity Studies of (.+−.)-9-fluoro-6,7,dihydro- . . . Agent" lyakuhin Kenkyu vol. 21, No. 4 (1990) pp. 636-646.
Nishijima, S. et al. "Sensitivity of *Staphyloccous aureus* and *Streptococcus pyogenes* isolated from Skin Infections in 1992 to . . . " Journal of Dermatology vol. 21 (1994) pp. 233-238 (XP000884342).
Udo, E..E. et al. "Emergence of High-Level Mupirocin Resistance in Methicillin-Resistant *Staphylococcus aureus* in Western Australia" J. of Hospital Infection vol. 26 (1994) pp. 157-165 (XP-000884369).
Abstract of Kurokawa, I. et al. "Antimicrobial Susceptibility of Propionibacterium Acnes Isolated From Vulgaris" European Journal of Dermatology vol. 9, No. 1 (1999) pp. 25-28.
Abstract of Gollnick, H. et al. "Topical Drug Treatment in Acne" Dermatology vol. 196, No. 1 (1998) pp. 119-125.
Abstract of Takahashi, N., et al. "Reduction of In Vitro Clastogenicity Induced by the Mixture of Optical Isomers of Nadifloxacin During Storage" Arzenimittel-Forschung vol. 45, No. 2 (1995) pp. 195.
Abstract of Takahashi, N. et al. "In Vitro Clastogenicity of Optical Isomers of Nadifoxacin" Arzneimittel-Forschung vol. 44, No. 11 (1994) pp. 1265-1268.
Abstract of Patel, M.V. "(S-(−)Nadifloxacin Oral Bioavailability and Bioefficacy in Mouse Model of Staphyloccal Septicemia" 39th ICAAC at San Diego Poster No. f0558 (Sep. 26-29, 1999).
Chemical Abstract: Doc. No. 123-334723 Vogt, K. et al "Antimicrobial Evaluation of Nadifloxacin (OPC-7251), A New Topical Quinolone, In . . . " Drugs vol. 49, Suppl. 2 (1995) pp. 266-268.

Chemical Abstract: Doc. No. 123:334716 Nishijima, S. et al. "In Vitro Activity of Nadifloxacin Both Methicillin-Susceptible and Resistant Clinical . . . " Drugs vol. 49, Suppl. 2 (1995) pp. 230-232.
Chemical Abstract: Doc. No. 124:21098 Bojar, R.A. et al. "Direct Analysis of Resistance in the Cutaneous Microflora During Treatment of Acne Vulgaris . . . " Drugs vol. 49, Supp. 2 (1995) pp. 164-167.
Chemical Abstract: Doc. No. 122:213914 "An Efficient Synthesis of a Key Intermediate Towards (S)-(−)-Nadifloxacin" Tetrahedron: Asymmetry vol. 6, No. 1 (1995) pp. 245-254.
Chemical Abstract: Doc. No. 119-4810 Vogt, K. et al.
Chemical Abstract: Doc. No. 113-231188 Morita, S. et al. "Synthesis and Antibacterial Activity of the Metabolites . . . " Chem Pharma. Bull. vol. 38, No. 7 (1990) pp. 2027-2029.
Chemical Abstract: Doc. No. 112:229223 Muto, N. et al. "Development of a Sensitive Enzyme Immunoassay for OPC-7251, A Novel Antimicrobial . . . " J. Immunoassay vol. 11, No. 1 (1990) pp. 1-16.
Chemical Abstract: Doc. No. 112::191305 Koike, M. et al. "High-Performance Liquid Chromatographic Procedure for the Determination . . . " J. Chromatogr. vol. 526, No. 1 (1990) pp. 235-239.
Chemical Abstract: Doc. No. 112-178631 Ishikawa, H. et al. "Studies on Antibacterial Agents: Synthesis of Substituted . . . " Chem. Pharma. Bull. vol. 37, No. 8 (1989) pp. 2103-2108.
Chemical Abstract: Doc. No. 112:52083 "Bacteriological Evaluation of OPC-7251, a new Pyridone Carboxylic Acid Antimicrobial Agent . . . " Chemotherapy vol. 37, No. 9 (1989) pp. 1160-1178.
Abstract of Komagata, Y. et al. "Fundamental Studies on Antibacterial Activity of Clindamycin Against Propionibacterium Acnes" Japanese J. Antibiotics vol. 51, No. 2, (1998) pp. 130-136.
Bundgaard H., Design of Prodrugs (1985) Elsevier pp. 1-3.
Morita, S., et al. Tetrahedron: Asymmetry (1995) 6(1) pp. 245-254.
Abstract: Nagao, T. et al. "Reproductive and Development Toxicity Studes of (.+−.) -9-fluoro-6,7-dihydro-8 . . . Administration" lyakuhin Kenkyu vol. 21, No. 4 (1990) pp. 647-662.
Abstract: Matsuzawa, A. et al. "Reproductive and Developmental Toxicity Studies of (.+..−)-9- fluoro . . . Adminstration" lyakuhin Kenkyu vol. 21, No. 4 (1990) pp. 663-670.
Abstract: Furukawa, M. et al. "Primary Skin Irritation, Four-Week Cumulative Skin Irritation, . . . 1% OPC-7251 Cream" lyakuhin Kenkyu vol. 21, No. 5 (1990) pp. 989-997.
Abstract: Nakagiri, N. et al. "Contact Sensitivity, Photocontact Sensitivity and Antigenicity Tests . . . Antibacterial Agent" lyakuhin Kenku=yu vol. 21, No. 6 (1990) p. 1144-1155.
Abstract: Aoki, M. et al. "Thirteen Week Percutaneous Toxicity and Four-Week Recovery Tests . . . (OPC-7251) in Dogs" lyakihin Kenkyu vol. 21, No. 6 (1990) pp. 1177-1202.
Abstract: Matsuzawa, A. et al. "Reproductive and Development Toxicity Studies of . . . Administration" lyakuhin Kenkyu vol. 22, No. 1 (1990) pp. 61-76.
Abstract: Bojar, R.A., et al. "Analysis of Resistance in the Cutaneous Microflora During Treatment of Acne . . . Erythromycin" J. of Investigative Dermatology vol. 103, No. 3 (1994) pp. 405.
Abstract: Bojar, R.A. et al. "Analysis of Resistance in the Cutaneous Microflora During Treatment ..2-Percent Erythromycin" J. of Investigate Dermatology vol. 103, No. 3 (1994) pp. 405.
Abstract: Haustein, U.F. et al. "Topical Quinolone Nadifloxacin (OPC-7251) in Bacterial Skin Disease . . . Testing" J. of Dermatological Treatment vol. 8, No. 2 (1997) pp. 87-92.
Abstract: Smith, C.M. et al. "Influence of Different Formulation on the Efficacy of Topical Nadifloxacin (OPC-7251)" J. of Investigative Dermatology vol. 108, No. 3 (1997) pp. 123.
Abstract: Hayakawa, R. et al. "Skin Safety Evaluation of Nadifloxain (OPC-7251)" Hifu vol. 40, No. 2 (1998) pp. 165-171.

* cited by examiner

ANTIBACTERIAL OPTICALLY PURE BENZOQUINOLIZINE CARBOXYLIC ACIDS, PROCESSES, COMPOSITIONS AND METHODS OF TREATMENT

This application is a continuation of application Ser. No. 09/566,875, now U.S. Pat. No. 7,247,642, filed on May 8, 2000, claims the benefit thereof and incorporates the same by reference. The nonprovisional application designated above, namely application Ser. No. 09/566,875, filed May 8, 2000, claims the benefit of U.S. Provisional Application No. 60/170,676 filed Dec. 14, 1999, and incorporates the same by reference.

FIELD OF THE INVENTION

The present invention relates to optically pure S-(−)-benzoquinolizine carboxylic acids, their derivatives, salts, pseudopolymorphs, polymorphs and hydrates thereof, substantially free of their R-(+)-isomers, to processes for preparation of the optically pure S-(−)-benzoquinolizine carboxylic acids, their derivatives, salts, pseudopolymorphs, polymorphs and hydrates thereof substantially free of their R-(+)-isomers, and to pharmaceutical compositions comprising the S(−)-benzoquinolizine carboxylic acids, their derivatives, salts, pseudopolymorphs, polymorphs and hydrates thereof. These compounds and compositions can be used to systemically and topically treat bacterial Gram-positive, Gram-negative and anaerobic infections, specially resistant Gram-positive organism infections, Gram-negative organism infections, mycobacterial infections and emerging nosocomial pathogen infections, while avoiding toxic effects associated with the administration of the racemic mixture of RS-(±)-benzoquinolizine carboxylic acid. The compounds and compositions of this invention can also be used to treat diseases and disorders caused by Gram-positive, Gram-negative and anaerobic bacteria, and diseases and disorders caused by resistant Gram-positive organisms, Gram-negative organisms, mycobacteria and nosocomial pathogens.

BACKGROUND OF THE INVENTION

Bacterial resistance to antibiotics is an increasingly recurrent phenomenon. Of grave concern has been the development of methicillin-resistant *Staphylococcus aureus* (MRSA) and methicillin-resistant *Streptococcus epidermidis* (MRSE) strains, which because of the phenomenon of cross-resistance, are now also resistant to the larger class of β-lactam antibiotics including the cephalosporins and carbapenems. Of even graver concern is the development of resistance in MRSA strains against the class of antibacterial agents known as fluoroquinolones. Several reports are known of MRSA strains displaying resistance to fluoroquinolone agents such as ciprofloxacin, sparfloxacin and even the more recently introduced trovafloxacin. In addition, for trovafloxacin and for newer introductions like grepafloxacin, moxifloxacin and gatifloxacin, a concern has been expressed about their checkered safety records. The use of trovafloxacin has been suspended or severely curtailed because of its association with liver side effects. Grepafloxacin was withdrawn worldwide because of severe cardiovascular side effects. The labelling on gatifloxacin and moxifloxacin warns that they may prolong the QTc interval on electrocardiograms in some patients.

The last line of defense against such fluoroquinolone-resistant MRSA strains is the class of glycopeptide antibiotics represented by vancomycin and teicoplanin. These glycopeptide antibiotics are, however, laden with several limitations. Vancomycin is encumbered with lack of oral bioavailability, nephrotoxic potential, toxic effects such as phlebitis and red-men syndrome. Moreover, the recent disturbing wide spread emergence of Vancomycin resistant enterococci (VRE) followed by the alarming reports of Vancomycin intermediate resistance *Staphylococcus aureus* (VISA) strains from Japan and USA have cast a shadow over the future of glycoside antibiotics in clinical practice. In time, there is a relatively wide-spread emergence of staphylococci, enterococci, pneumococci and streptococci, which have become resistant to currently used first-and second-line antibacterial agents such as penicillin, oxacillin, vancomycin and erythromycin (SENTRY Programme: Antimicrobial Agents & Chemotherapy 42 1762-1770, 1998).

Also, for primary skin infections such as impetigo and folliculitis, and for secondary infections in humans such as infected dermatitis, wounds and burns, as well as to eliminate nasal carriage of MRSA in healthcare workers and patients, a special antibiotic used topically is Mupirocin. Mupirocin has high in vitro anti-staphylococcal and anti-streptococcal activity. There has, however, been an increase of organisms, specially staphylococci, developing resistance to Mupirocin. The emergence of Mupirocin-resistant Methicillin-resistant *Staphylococcus aureus* (MRSA) in infected patients in different countries like Canada, Western Australia, UK, Spain and Switzerland is described in different references in the medical and scientific literature viz. J. Hosp. Infect. 39(1), 19-26 (1998); J. Hosp. Infect. 26(3), 157-165 (1994); Infect Control Hosp Epidemiol 17(2), 811-813 (1996); 38$^{th}$ Annual ICAAC Abstract C-75, 90 (1998); 38$^{th}$ ICAAC Abstract 12-25, 507 (1998).

Furthermore, Gram-positive pathogens such as Staphylococci, enterococci and Gram-negative pathogens *E. coli, Klebsiella, Proteus, Serratia, Citrobacter* and *Pseudomonas*, frequently encountered in urinary tract infections are susceptible to the known fluoroquinolones, such as ciprofloxacin, levofloxacin, ofloxacin and norfloxacin. The potency of these fluoroquinolones, however, markedly deteriorates under the acidic conditions likely to be encountered in urinary tract infections, rendering them inadequate.

Furthermore, multidrug-resistant (MDR) mycobacterial strains have emerged displaying resistance to first-line anti-mycobacterial agents such as rifampicin, pyrazinamide and INH etc. thus severely curtailing therapeutic options available for the management of infections due to such strains. Usually, the antimycobacterial drug regimen involves treatment spread over several months, and hence the drug has to be tolerated well by the patients. Among the fluoroquinolone antibiotics, sparfloxacin is reported to be highly active against mycobacteria. It is not quite suitable, however, for long-term therapy because of its potential to cause phototoxic side effects in humans and laboratory animals such as mice and guinea-pigs.

Furthermore, in the worldwide management of nosocomial infections, besides the problematic strains of staphylococci and enterococci, including MRSA, strains of Chryseobacteria have recently emerged as new members of nosocomial pathogens causing neonatal meningitis and pneumonia, as well as sepsis, in immuno-compromised patients being treated in intensive care units. Chryseobacteria are intrinsically resistant to β-lactam antibiotics including third-generation cephalosporins and carbapenems. These factors reduce the treatment options available to the clinicians.

The highly pressing need for other agents and methods of treatment for infections arising from such emerging resistant microorganisms, Gram-negative pathogens in acidic environments, mycobacteria and nosocomial pathogens thus assumes great significance.

Among other agents, one particular class of compounds the benzoquinolizine carboxylic acids are of particular relevance. Nadifloxacin is an example of a benzoquinolizine carboxylic acid. Nadifloxacin is racemic [(±)-9-fluoro-8-(4-hydroxypiperidin-1-yl)-5-methyl-6,7-dihydro-1-oxo-1H-5H-benzo[i,j]quinolizine-2-carboxylic acid and is disclosed in JP Patent No. 58,90,511 and U.S. Pat. No. 4,399,134. Nadifloxacin has an asymmetric carbon atom at the 5-position thereof. RS-(±)-Nadifloxacin comprises two optically active isomers. In describing an optically active compound, the prefixes R and S or D and L are used to denote the absolute configuration of the molecule about its chiral centre(s). The prefixes (+) and (−) or d and l are employed to designate the sign of rotation of plane-polarized light by the compound, with (−) or l meaning that the compound is levorotatory. A compound prefixed with (+) or d is dextrorotatory. Compounds having a single chiral centre exist as a pair of enantiomers, which are identical except that they are non-superimposable mirror images of one another. A one-to-one mixture of enantiomers is often referred to as a racemic mixture. Racemic RS-(±)-Nadifloxacin derives its biological activity primarily from the S-(−)-enantiomer. The optically active S-(−)-Nadifloxacin$[\alpha]^{20}_D$=−312.0 is obtained as disclosed in Chem. Pharm. Bull 44 (1996), page nos. 642-5 and Jpn. Kokai Tokyo Koho JP 63,192,753. The optically active R-(+)-Nadifloxacin, $[\alpha]^{20}_D$=+312.0, is obtained as disclosed in Jpn. Kokai Tokyo Koho JP 63,192,753. Pharmaceutical compositions of RS-(±)-Nadifloxacin are disclosed in U.S. Pat. No. 4,399,134 and U.S. Pat. No. 4,552,879. Although these cited patents disclose compositions of RS-(±)-Nadifloxacin for oral, parenteral and topical use, the only commercial product containing RS-(±)-Nadifloxacin as an active antibacterial compound is the commercial product named Acuatim®. Acuatim® is available as a cream and a lotion and incorporates racemic RS-(±)-Nadifloxacin as 1% of its composition for the topical treatment of acne. Acuatim® has several drawbacks. It is intended only for topical use and is registered only for the treatment of acne caused by *Propionibacterium* species. One report has appeared on the in-vitro activity of the fluoroquinolone, Nadifloxacin, against methicillin resistant isolates of *Staphylococcus aureus* from patients with skin infections (see Nishijima et al., Drugs 49 (Suppl.) 230-232, 1995). There is no report of RS-(±)-Nadifloxacin being approved for systemic use against any microbial infections, whether for sensitive or resistant microbial strains.

S-(−)-Nadifloxacin is reported in Chem. Pharm, Bull 44 (1996) pages Nos. 421-423 to be approximately twice as active in-vitro as racemic Nadifloxacin against Gram-positive and Gram-negative bacteria. There is no previous report, however, of the activity of S-(−)-Nadifloxacin in in-vivo systems against Gram-positive bacteria, Gram-negative bacteria, anaerobes, mycobacteria and emerging nosocomial pathogens.

RS-(±)-Nadifloxacin is reported to exist in two crystalline forms, one as an anhydrate and the other as a hemihydrate (M. Kido and K. Hashimoto, Chem. Pharm. Bull, 42, 872 (1994)). There is no previous report, however, of any hydrate forms of S-(−)-Nadifloxacin, although a non-hydrate form is reported (K. Hashimoto et al., Chem. Pharm. Bull., 44,642 (1996)).

There is no previous report of the utility of optically pure benzoquinolizine carboxylic acids, their derivatives, salts, pseudopolymorphs, polymorphs and hydrates thereof of the invention in pharmaceutical compositions. There is also no previous report of the systemic or topical use of optically pure benzoquinolizine carboxylic acids, their derivatives, salts and hydrates thereof of the invention, either alone or in compositions for treatment of microbial infections diseases or disorders.

Our pending PCT patent application No. PCT/IN99/00016 filed on May 7, 1999 describes optically pure and racemic benzoquinolizine carboxylic acids, derivatives and salts thereof for treatment of infections caused by Mupirocin-resistant bacterial strains such as Mupirocin-resistant staphylococci, Mupirocin-resistant streptococci and other Mupirocin-resistant Gram-positive and Mupirocin-resistant Gram-negative bacteria, and for treatment of dermal diseases such as impetigo, folliculitis, infected dermatitis, wounds and burns. The subject matter of PCT application PCT/IN99/00016 is incorporated herein by reference.

SUMMARY OF THE INVENTION

The present inventors obtained optically pure isomers of Nadifloxacin and have conducted extensive studies to show that:
1. S-(−)-Nadifloxacin is found to exist not only as an anhydrate but also as three new different hydrates designated as S-(−)-Nadifloxacin.$nH_2O$, wherein n is equal to 0.2, 0.5 or 0.75. Among these forms of the anhydrate and the three hydrates, S-Nadifloxacin.0.2 $H_2O$ is now specifically found to be preferred as a stable, non-hygroscopic crystalline modification which is distinguished by an increased stability, neither losing the water content therein nor absorbing moisture over a wide range of ambient relative humidity conditions. In contrast, moisture absorption by the anhydrate varies according to its method of preparation and the relative humidity conditions to which it is subjected. The other two hydrates, viz. the hemihydrate, S-(−)-Nadifloxacin.0.5$H_2O$ and the hemisesquihydrate, S-nadifloxacin.0.75$H_2O$, both revert to S-nadifloxacin.0.2$H_2O$ when dried in vacuo at ambient temperature conditions.

S-(−)-Nadifloxacin.0.2$H_2O$ has considerable advantages over the anhydrate, the hemihydrate and the hemisesquihydrate in storage and handling and in the preparation of medicament forms. In particular, specially in tropical and subtropical climates, where the ambient humidity is usually greater than 70%, difficulty is encountered in the storage and handling of the anhydrate. In the preparation of pharmaceutical preparations, such as tablets, containing the anhydrate, the operations must be carried out with attention to absorption or desorption of water of crystallisation. More specifically, a room in which to handle the anhydrate must be kept at low humidity and conversely, a room in which to handle the hemihydrate and hemisesquihydrate must be kept at low temperatures and high humidity. Unless these conditions are provided, these compounds or preparations containing these compounds would change in weight, and thus would not serve for practical purposes and would lose their commercial value. By using a stable non-hygroscopic, free-flowing active compound, as is provided by S-(−)-Nadifloxacin 0.2 $H_2O$, a satisfactory dosing consistency and accuracy is achieved during the preparation of medicaments, which increases safety and therefore minimizes the risk to the patient.
2. Crystalline salts of S-(−)-Nadifloxacin, especially sodium, potassium, and arginine salts, and hydrates thereof have been identified with increased aqueous solubility over S-(−)-Nadifloxacin, and consequently with superior properties for use in the preparation of parenteral formulations, and with advantages of improved oral bioavailability in solid oral dosage forms.

3. Derivatives of S-(−)-Nadifloxacin are identified at the sites of the 2-COOH function and the 4'-hydroxy moiety of the 9-(4'-hydroxypiperidino) group respectively, and salts and hydrates thereof.

4. Processes are described to obtain the optically pure benzoquinolizine carboxylic acids of the invention, the derivatives, salts, pseudopolymorphs, polymorphs and hydrates thereof mentioned under items 1-3 above and as described in detail below.

5. RS-(±)-Nadifloxacin, S-(−)-Nadifloxacin and optically pure benzoquinolizine carboxylic acids, the derivatives, salts, pseudopolymorphs, polymorphs and hydrates thereof have high activity against Mupirocin-resistant microbial strains such as Mupirocin-resistant staphylococci, Methicillin-resistant *staphylococcus aureus* and Quinolone-resistant *Staphylococcus aureus*, coagulase negative staphylococci, such as Methicillin-resistant *Staphylococcus epidermidis* (MRSE), enterococci, beta-hemolytic streptococci and viridans group of streptococci.

6. RS-(±)-Nadifloxacin, S-(−)-Nadifloxacin and optically pure benzoquinolizine carboxylic acids, the derivatives, salts, pseudopolymorphs, polymorphs and hydrates thereof have activity against mycobacteria and newly emerging nosocomial pathogens such as *Chryseobacterium meningosepticum*.

7. S-(−)-Nadifloxacin and optically pure benzoquinolizine carboxylic acids, the derivatives, salts, pseudopolymorphs, polymorphs and hydrates thereof have 2-4 times higher antimicrobial activity than racemic-Nadifloxacin against Mupirocin-resistant staphylococci, Methicillin-resistant *Staphylococcus aureus* (MRSA), Quinolone-resistant *Staphylococcus aureus*, coagulase negative staphylococci, such as Methicillin-resistant *Staphylococcus epidermidis* (MRSE), enterococci, betahemolytic streptococci and viridans group of streptococci, mycobacteria and newly emerging nosocomial pathogens such as *Chryseobacterium meningosepticum*.

8. S-(−)-Nadifloxacin and optically pure benzoquinolizine carboxylic acids, the derivatives, salts, pseudopolymorphs, polymorphs and hydrates thereof are not only bacteriostatic but also bactericidal towards Mupirocin-resistant staphylococci, Methicillin-resistant *Staphylococcus aureus* (MRSA), Quinolone-resistant *Staphylococcus aureus*, coagulase negative staphylococci, such as Methicillin-resistant *Staphylococcus epidermidis* (MRSE), enterococci at concentrations 2-4 times lower than that of RS-(±)-Nadifloxacin.

9. S-(−)-Nadifloxacin and optically pure benzoquinolizine carboxylic acids, the derivatives, salts, pseudopolymorphs, polymorphs and hydrates thereof have 2-4 times higher antimicrobial activity against Gram-positive pathogens such as staphylococci and enterococci and Gram-negative pathogens such as *E. coli, Klebsiella, Proteus, Serratia* and *Citrobacter* in the acidic environments encountered in infection such as urinary tract infections.

10. S-(−)-Nadifloxacin, its derivatives, salts, pseudopolymorphs, polymorphs and hydrates thereof have high potency against efflux pump-bearing *Staphylococcus* strains and are thus of unique value in treating infections caused by antibiotic-resistant microorganisms for which the resistance mechanism is due to the presence of efflux pumps.

11. S-(−)-Nadifloxacin, its derivatives, salts, pseudopolymorphs, polymorphs and hydrates thereof have high propensity to display resistance to resistance development, which has been shown in studies involving sequential transfers/passages of a *S. aureus* strain through respective drug containing media.

12. The acute intravenous toxicity of S-(−)-Nadifloxacin and its arginine salt is significantly lower than RS-(±)-Nadifloxacin (Biological Example 3).

13. S-(−)-Nadifloxacin, its derivatives, salts and hydrates thereof have a favorable toxicity profile in comparison with other fluoroquinolone drugs in clinical use in respect of cytotoxic effect on various cell lines (Biological Example 4), phototoxicity (vide infra) and cardiotoxicity.

14. The oral bioavailability of S-(−)-Nadifloxacin is 2-times higher than that of RS-(±)-Nadifloxacin (Biological Example 5).

Through their extensive studies, the present inventors have shown for the first time a novel expanded set of clinically desired antimicrobial attributes of efficacy and safety of S-(−)-Nadifloxacin, which have been not reported in the literature since the first disclosure of S-(−)-Nadifloxacin in JP 63, 192, 753 about twelve years ago and of RS-(±)-Nadifloxacin in JP 58,90,511 about twenty years ago. New hydrates, salts, derivatives, pseudopolymorphs, polymorphs and compositions of S-(−)-Nadifloxacin have also been identified by the present inventors, which have in addition to their biological properties mentioned above, newer physico-chemical properties, thus permitting their utility in a clinical and commercial exploitation in newer compositions for newer diseases and newer methods of systemic and topical treatment that were hitherto not possible.

It is, thus, an object of the present invention to provide S-(−)-optically pure benzoquinolizine carboxylic acids, their derivatives, salts, pseudopolymorphs, polymorphs and hydrates thereof, of the formula I, substantially free of their R-(+)-isomers.

Formula I

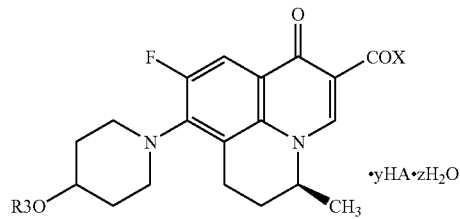

It is another object of the present invention to provide a process or processes for preparing the novel optically pure S-(−)-optically pure benzoquinolizine carboxylic acids, their derivatives, salts, pseudopolymorphs, polymorphs and hydrates thereof, of the formula I.

A further object is to provide pharmaceutical compositions comprising optically pure S-(−)-benzoquinolizine carboxylic acids, the derivatives, pseudopolymorphs, hydrates and salts thereof as potent antibacterial agents for treating systemic and topical bacterial infections, especially infections caused by resistant Gram-positive, sensitive and resistant Gram-negative organisms, mycobacterial infections and nosocomial pathogen infections while avoiding the toxic effects associated with the administration of their R-(+)-isomers.

Another object of this inventions relates to a method of treatment of infections caused by Mupirocin-resistant bacterial strains such as Mupirocin-resistant staphylococci, Mupirocin-resistant streptococci and other Mupirocin-resistant Gram-positive and Mupirocin-resistant Gram-negative bacteria, and of dermal diseases and disorders such as impetigo, folliculitis, infected dermatitis, wounds and burns. Treatment comprises oral, parenteral, administration and/or topical application of an effective amount of a composition of S-(−)-Nadifloxacin or optically pure benzoquinolizine carboxylic acids, their derivatives, salts, pseudopolymorphs, polymorphs and hydrates thereof of formula I, or of a composition of RS-(+)-Nadifloxacin and pharmaceutically acceptable salts thereof.

A further object of the invention includes methods for treating the infections in humans and animals caused by Gram-positive, Gram-negative and anaerobic bacteria, resistant Gram-positive organism such as Methicillin-resistant *Staphylococcus aureus* (MRSA), Quinolone-resistant *Staphylococcus aureus*, coagulase negative staphylococci, such as Methicillin-resistant *Staphylococcus epidermidis* (MRSE), enterococci, betahemolytic streptococci and viridans group of streptococci, mycobacteria and newly emerging nosocomial pathogens such as *Chryseobacterium meningosepticum*, and Gram-negative pathogens such as *E. coli, Klebsiella, Proteus, Serratia Citrobacter* and *Pseudomonas*, while avoiding the toxic effects that are associated with the racemic mixture of Nadifloxacin by administering systemically or topically S-(−)-Nadifloxacin or optically pure S-(−)-benzoquinolizine carboxylic acids, their derivatives, salts, pseudopolymorphs, polymorphs and hydrates thereof to the affected human or animal.

BRIEF DESCRIPTION OF THE DRAWINGS

For a thorough understanding of the nature and objects of the invention, reference should be made to the following detailed description taken in connection with the accompanying drawings in which 1.

DETAILED DESCRIPTION OF THE INVENTION

Figure 1:
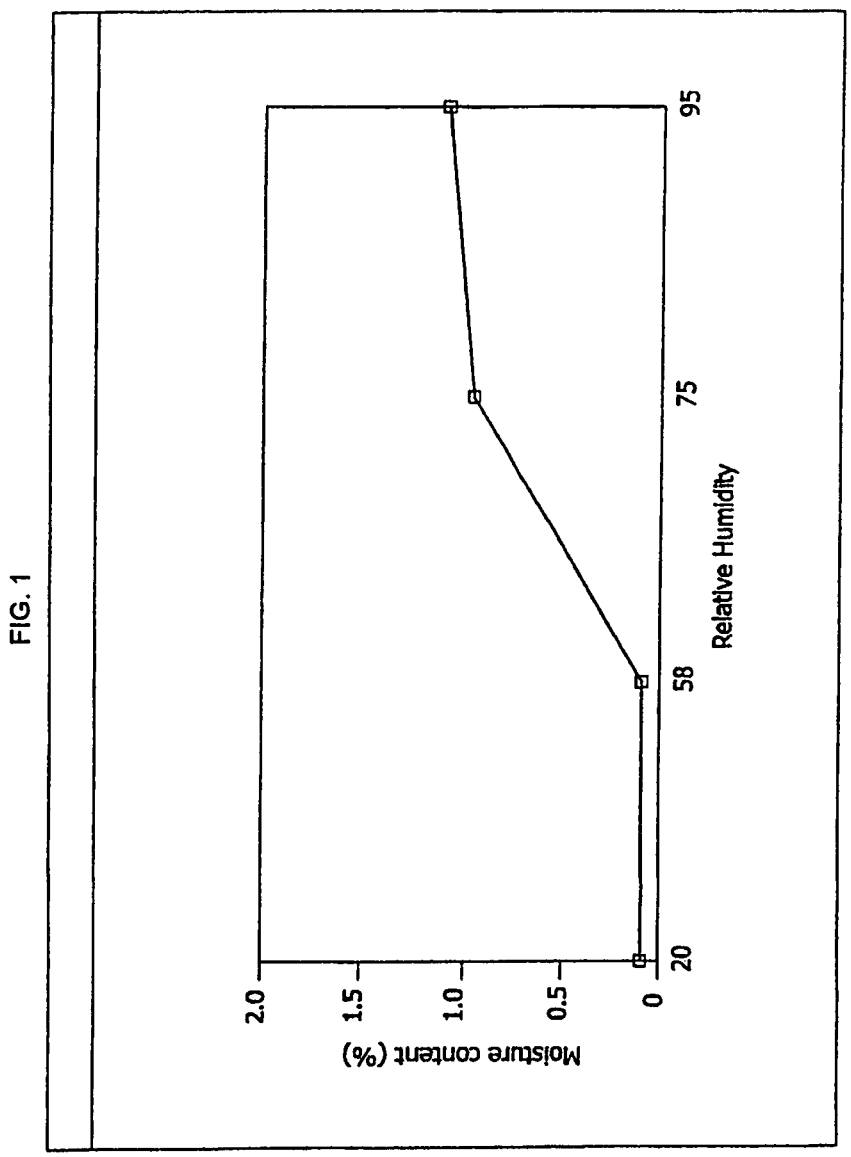
FIG. 1 represents the moisture content of S-(−)-9-fluoro-6,7-dihydro-8-(4-hydroxypiperidin-1-yl)-5-methyl-1-oxo-1H,5H-benzo[i,j]quinolizine-2-carboxylic acid anhydrate at a relative humidity of 20% to 95%.
2.

This invention relates to S-(−)-optically pure benzoquinolizine carboxylic acids, of formula I,

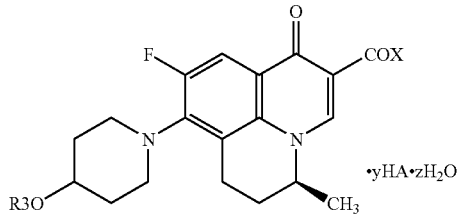

Formula I and their pharmaceutically acceptable salts, derivatives, pseudopolymorphs, polymorphs and hydrates, substantially free of their R-(±)-isomers;

wherein

X is $OR_1$, wherein $R_1$ is hydrogen, a pharmaceutically acceptable cation, such as those of alkali metals such as lithium, sodium, potassium; alkaline earth metals such as magnesium or calcium, aluminum, ammonium or substituted ammonium salts; choline or organic amines such as diethanolamine, guanidine or heterocyclic amines such as piperidine, hydroxyethylpyrrolidine, hydroxyethylpiperidine, morpholine, piperazine, N-methyl piperazine and the like or basic amino acids such as optically pure and racemic isomers of arginine, lysine, histidine, tryptophan and the like;

or $R_1$ is $C_1$-$C_6$ alkyl, such as straight chain or branched chain aliphatic residues such as methyl, ethyl, propyl, isopropyl, butyl, isobutyl, pentyl, hexyl and their branched chain isomers;

or $R_1$ is —$(CH_2)_n$—$CHR_4$—$OOCR_5$, wherein $R_4$=H, or $CH_3$; n=0-3 and $R_5$=$C_2H_5$ or $C(CH_3)_3$, $R_1$ is a group such as acetoxymethyl, pivaloyloxymethyl, pivaloyloxyethyl group;

or $R_1$ is

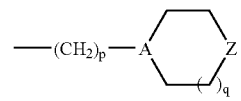

wherein A=CH or N, and when A=CH, Z=NH or $NCH_3$, and when A=N, Z=CH, O, N, S, or $NCH_3$; p=0-2; q=0-2, wherein $R_1$ is a group such as N-methylpiperidin-4-yl, pyrrolidin-2-yl-ethyl, piperidin-2-yl-ethyl, or morpholin-2-yl-ethyl;

or X is $NHR_2$, wherein $R_2$ is hydrogen or $NHR_2$ is the residue of one of the 20 naturally occurring amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof, or the racemic mixtures thereof, R₃ is hydrogen, $C_1$-$C_6$ alkyl ($C_1$-$C_6$ alkyl is defined as above), glycosyl, aralkyl such as benzyl, $C_1$-$C_6$ alkanoyl such as acetyl, propionyl, pivaloyl; or aminoalkanoyl. The amino alkanoyl group may be an amino acid residue derived from one of the 20 naturally occurring amino acids or the optically active isomers thereof, or the racemic mixtures thereof. The amino acid residue is derived from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. R₃ may also be $C_6H_{11}O_6$, $PO_3H_2$ or $SO_3H$ thus giving respectively, esters with gluconic acid, phosphoric acid derivatives, or sulphuric acid derivatives of the compounds.

y denotes an integer from 0 to 3 and any fractional numbers therein depending on the moles of acid added to the basic molecule;

z denotes moles of water, for example 0, 0.2, 0.25, 0.5, 0.75, 1, 1.25, 1.5, 2, 3, etc; and HA represents an acid as defined below for acid addition salts.

Pharmaceutically acceptable salts are those salts already included by definition of the symbol X in Formula I. In addition, in view of the basic character of the compounds of Formula I and of the basic amino acids used in the preparation of derivatives it is possible to make acid addition salts. Also, because of the acidic character introduced in the derivatives of Formula I, it is also possible to make basic or alkali addition salts of the compounds of Formula I. Preferred acid addition salts are those of hydrochloride, hydrobromide, hydroiodide, sulphate, phosphate and salts of organic acids such as acetate, lactate, succinate, oxalate, maleate, fumarate, malate, tartrate, citrate, ascorbate, cinnamate, gluconate, benzoate, methane sulfonate and p-toluene sulfonate. Preferred alkali addition salts are lithium, sodium, and potassium salts, and alkaline earth salts are magnesium, and calcium salts.

Specific compounds of the invention are:
1. S-(−)-9-fluoro-6,7-dihydro-8-(4-hydroxypiperidin-1-yl)-5-methyl-1-oxo-1H,5H-benzo[i,j]quinolizine-2-carboxylic acid.
2. S-(−)-9-fluoro-6,7-dihydro-8-(4-hydroxypiperidin-1-yl)-5-methyl-1-oxo-1H,5H-benzo[i,j]quinolizine-2-carboxylic acid 0.2 H₂O.
3. S-(−)-9-fluoro-6,7-dihydro-8-(4-hydroxypiperidin-1-yl)-5-methyl-1-oxo-1H,5H-benzo[i,j]quinolizine-2-carboxylic acid 0.5 H₂O.
4. S-(−)-9-fluoro-6,7-dihydro-8-(4-hydroxypiperidin-1-yl)-5-methyl-1-oxo-1H,5H-benzo[i,j]quinolizine-2-carboxylic acid 0.75 H₂O.
5. S-(−)-9-fluoro-6,7-dihydro-8-(4-hydroxypiperidin-1-yl)-5-methyl-1-oxo-1H,5H-benzo[i,j]quinolizine-2-carboxylic acid sodium salt.
6. S-(−)-9-fluoro-6,7-dihydro-8-(4-hydroxypiperidin-1-yl)-5-methyl-1-oxo-1H,5H-benzo[i,j]quinolizine-2-carboxylic acid, sodium salt monohydrate.
7. S-(−)-9-fluoro-6,7-dihydro-8-(4-hydroxypiperidin-1-yl)-5-methyl-1-oxo-1H,5H-benzo[i,j]quinolizine-2-carboxylic acid, potassium salt monohydrate.
8. S-(−)-9-fluoro-6,7-dihydro-8-(4-hydroxypiperidin-1-yl)-5-methyl-1-oxo-1H,5H-benzo[i,j]quinolizine-2-carboxylic acid, arginine salt.
9. S-(−)-9-fluoro-6,7-dihydro-8-(4-hydroxypiperidin-1-yl)-5-methyl-1-oxo-1H,5H-benzo[i,j]quinolizine-2-carboxylic acid, arginine salt 0.25 H₂O.
10. S-(−)-9-fluoro-6,7-dihydro-8-(4-hydroxypiperidin-1-yl)-5-methyl-1-oxo-1H,5H-benzo[i,j]quinolizine-2-carboxylic acid, arginine salt .0.75 H₂O.
11. S-(−)-9-fluoro-6,7-dihydro-8-(4-hydroxypiperidin-1-yl)-5-methyl-1-oxo-1H,5H-benzo[i,j]quinolizine-2-carboxylic acid, lysine salt monohydrate.
12. S-(−)-9-fluoro-6,7-dihydro-8-(4-hydroxypiperidin-1-yl)-5-methyl-1-oxo-1H,5H-benzo[i,j]quinolizine-2-carboxylic acid, histidine salt 0.2 H₂O.
13. S-(−)-9-fluoro-6,7-dihydro-8-(4-hydroxypiperidin-1-yl)-5-methyl-1-oxo-1H,5H-benzo[i,j]quinolizine-2-carboxylic acid, hydroxyethyl pyrrolidine salt.
14. S-(−)-9-fluoro-6,7-dihydro-8-(4-hydroxypiperidin-1-yl)-5-methyl-1-oxo-1H,5H-benzo[i,j]quinolizine-2-carboxylic acid, diethanolamine salt.
15. S-(−)-9-fluoro-6,7-dihydro-8-(4-hydroxypiperidin-1-yl)-5-methyl-1-oxo-1H,5H-benzo[i,j]quinolizine-2-carboxylic acid, choline salt and its hydrates.
16. Carboxymethyl S-(−)-9-fluoro-6,7-dihydro-8-(4-hydroxypiperidin-1-yl)-5-methyl-1-oxo-1H,5H-benzo[i,j]quinolizine-2-carboxylate sodium salt.
17. Acetoxymethyl S-(−)-9-fluoro-6,7-dihydro-8-(4-hydroxypiperidin-1-yl)-5-methyl-1-oxo-1H,5H-benzo[i,j]quinolizine-2-carboxylate.
18. Propionoxymethyl S-(−)-9-fluoro-6,7-dihydro-8(4-hydroxypiperidin-1-yl)-5-methyl-1-oxo-1H,5H-benzo[i,j]quinolizine-2-carboxylate.
19. Pivaloyloxymethyl S-(−)-9-fluoro-6,7-dihydro-8-(4-hydroxypiperidin-1-yl)-5-methyl-1-oxo-1H,5H-benzo[i,j]quinolizine-2-carboxylate.
20. Pivaloyloxyethyl S-(−)-9-fluoro-6,7-dihydro-8-(4-hydroxypiperidin-1-yl)-5-methyl-1-oxo-1H,5H-benzo[i,j]quinolizine-2-carboxylate.
21. N-methylpiperidin-4-yl S-(−)-9-fluoro-6,7-dihydro-8-(4-hydroxy piperidin-1-yl)-5-methyl-1-oxo-1H,5H-benzo[i,j]quinolizine-2-carboxylate.
22. Pyrrolidin-2-yl-ethyl S-(−)-9-fluoro-6,7-dihydro-8-(4-hydroxy piperidin-1-yl)-5-methyl-1-oxo-1H,5H-benzo[i,j]quinolizine-2-carboxylate.
23. Piperidin-2-yl-ethyl S-(−)-9-fluoro-6,7-dihydro-8-(4-hydroxypiperidin-1-yl)-5-methyl-1-oxo-1H,5H-benzo[i,j]quinolizine-2-carboxylate.
24. Morpholin-2-yl-ethyl S-(−)-9-fluoro-6,7-dihydro-8-(4-hydroxy piperidin-1-yl)-5-methyl-1-oxo-1H,5H-benzo[i,j]quinolizine-2-carboxylate.
25. 9-fluoro-8(4-hydroxypiperidin-1-yl)-(5S)-methyl-6,7-dihydro-1-oxo-1H,5H-benzo[i,j]quinolizine-2-[2(S)-amino-1,5-pentanedioic acid]carboxamide, disodium salt.
26. 9-fluoro-8-{4-hydroxypiperidin-1-yl}-5(S)-methyl-6,7dihydro-1-oxo-1H,5H-benzo[i,j]quinolizine-2-[2(S)-amino-3-imidazolylpropionic acid] carboxamide hydrochloride.
27. S-(−)-9-fluoro-6,7-dihydro-8-(4-methoxypiperidin-1-yl)-5-methyl-1-oxo-1H,5H-benzo[i,j]quinolizine-2-carboxylic acid.
28. S-(−)-9-fluoro-6,7-dihydro-8-(4-[(β-D-tetraacetylglucopyranosyl)oxy]-piperidin-1-yl)-5-methyl-1-oxo-1H,5H-benzo[i,j]quinolizine-2-carboxylic acid.
29. S-(−)-9-fluoro-6,7-dihydro-8-(4-[(β-D-glucopyranosyl)oxy]-piperidin-1-yl)-5-methyl-1-oxo-1H,5H-benzo[i,j]quinolizine-2-carboxylic acid.
30. S-(−)-9-fluoro-6,7-dihydro-8-(4-acetoxypiperidin-1-yl)-5-methyl-1-oxo-1H,5H-benzo[i,j]quinolizine-2-carboxylic acid.
31. S-(−)-9-fluoro-6,7-dihydro-8-(4-pivaloyloxypiperidin-1-yl)-5-methyl-1-oxo-1H,5H-benzo[i,j]quinolizine-2-carboxylic acid.
32. S-(−)-9-fluoro-8-[4-(phosphonoxy)-1-piperidin-1-yl)-5-methyl-1-oxo-1H,5H-benzo[i,j]quinolizine-2-carboxylic acid.

33. 8-{4-[2(S)-Amino-propionyloxy]piperidin-1-yl}-9-fluoro-5(S)-methyl-6,7-dihydro-1-oxo-1H,5H-benzo[i,j]quinolizine-2-carboxylic acid.
34. 8-{4-[2(S)-Amino-propionyloxy]piperidin-1-yl}-9-fluoro-5(S)-methyl-6,7-dihydro-1-oxo-1H,5H-benzo[i,j]quinolizine-2-carboxylic acid, hydrochloride.
35. 8-{4-[2(R)-Amino-propionyloxy]piperidin-1-yl}-9-fluoro-5(S)-methyl-6,7-dihydro-1-oxo-1H,5H-benzo[i,j]quinolizine-2-carboxylic acid.
36. 8-{4-[2(R)-Amino-propionyloxy]piperidin-1-yl}-9-fluoro-5(S)-methyl-6,7-dihydro-1-oxo-1H,5H-benzo[i,j]quinolizine-2-carboxylic acid, acetate.
37. 8-{4-[2(RS)-Amino-propionyloxy]piperidin-1-yl}-9-fluoro-5(S)-methyl-6,7-dihydro-1-oxo-1H,5H-benzo[i,j]quinolizine-2-carboxylic acid.
38. 8-{4-[(2S)-amino-propionyl-2S)-aminopropionyloxy]piperidin-1-yl}-9-fluoro-5(S)-methyl-6,7-dihydro-1-oxo-1H,5H-benzo[i,j]quinolizine-2-carboxylic acid hydrochloride.
39. 8-{4[(2R)-Amino-propionoyl-(2R)-aminopropionyloxy]piperidin-1-yl}-9-fluoro-(5S)-methyl-6,7dihydro-1-oxo-1H,5H-benzo[i,j]quinolizine-2-carboxylic acid.
40. 8-{4[(2R)-Amino-propionoyl-(2R)-aminopropionyloxy]piperidin-1-yl}-9-fluoro-(5S)-methyl-6,7dihydro-1-oxo-1H,5H-benzo[i,j]quinolizine-2-carboxylic acid hydrochloride.
41. 8-{4[(2R)-Amino-propionoyl-(2R)-aminopropionyloxy]piperidin-1-yl}-9-fluoro-(5S)-methyl-6,7dihydro-1-oxo-1H,5H-benzo[i,j]quinolizine-2-carboxylic acid acetate.
42. 8-{4[(2S)-Methylamino-propionyloxy]piperidin-1-yl}-9-fluoro-(5S)-methyl-6,7dihydro-1-oxo-1H,5H-benzo[i,j]quinolizine-2-carboxylic acid.
43. 8-{4[(2S)-Methylamino-propionyloxy]piperidin-1-yl}-9-fluoro-(5S)-methyl-6,7dihydro-1-oxo-1H,5H-benzo[i,j]quinolizine-2-carboxylic acid and hydrochloride.
44. 8-{4[2(S)-amino-3-carboxypropionyloxy]piperidin-1-yl}-9-fluoro-5(S)-methyl-6,7dihydro-1-oxo-1H,5H-benzo[i,j]quinolizine-2-carboxylic acid hydrochloride.
45. 8-{4[2(S)-amino-3-phenylpropionyloxy]piperidin-1-yl}-9-fluoro-5(S)-methyl-6,7dihydro-1-oxo-1H,5H-benzo[i,j]quinolizine-2-carboxylic acid hydrochloride.
46. 8-{4[2(R)-amino-3-phenylpropionyloxy]piperidin-1-yl}-9-fluoro-5(S)-methyl-6,7dihydro-1-oxo-1H,5H-benzo[i,j]quinolizine-2-carboxylic acid hydrochloride.
47. 8-{4[2(R)-amino-3-phenylpropionyloxy]piperidin-1-yl}-9-fluoro-5(S)-methyl-6,7dihydro-1-oxo-1H,5H-benzo[i,j]quinolizine-2-carboxylic acid acetate.
48. 8-{4[(2S)-Amino-3-methylbutanoyloxy]piperidin-1-yl}-9-fluoro-(5S)-methyl-6,7dihydro-1-oxo-1H,5H-benzo[i,j]quinolizine-2-carboxylic acid.
49. 8-{4[(2S)-Amino-3-methylbutanoyloxy]piperidin-1-yl}-9-fluoro-(5S)-methyl-6,7dihydro-1-oxo-1H,5H-benzo[i,j]quinolizine-2-carboxylic acid and hydrochloride.
50. 8-{4-[2(S)-Amino-4-methylpentanoyloxy]piperidin-1-yl}-9-fluoro-5(S)-methyl-6,7dihydro-1-oxo-1H,5H-benzo[i,j]quinolizine-2-carboxylic acid.
51. 8-{4-[2(S)-Amino-4-methylpentanoyloxy]piperidin-1-yl}-9-fluoro-5(S)-methyl-6,7-dihydro-1-oxo-1H,5H-benzo[i,j]quinolizine-2-carboxylic acid, hydrochloride.
52. 8-{4[(2R)-Amino-4-methylpentanoyloxy]piperidin-1-yl}-9-fluoro-(5S)-methyl-6,7dihydro-1-oxo-1H,5H-benzo[i,j]quinolizine-2-carboxylic acid.
53. 8-{4[(2R)-Amino-4-methylpentanoyloxy]piperidin-1-yl}-9-fluoro-(5S)-methyl-6,7dihydro-1-oxo-1H,5H-benzo[i,j]quinolizine-2-carboxylic acid and hydrochloride.
54. 8-{4-[2(S),6-Diaminohexanoyloxy]piperidin-1-yl}-9-fluoro-5(S)-methyl-6,7-dihydro-1-oxo-1H,5H-benzo[i,j]quinolizine-2-carboxylic acid.
55. 8-{4-[2(S),6-Diaminohexanoyloxy]piperidin-1-yl}-9-fluoro-5(S)-methyl-6,7-dihydro-1-oxo-1H,5H-benzo[i,j]quinolizine-2-carboxylic acid, dihydrochloride.
56. 8-{4[(2S)-Amino-5-nitroguanidino-butanoyloxy]piperidin-1-yl}-9-fluoro-(5S)-methyl-6,7dihydro-1-oxo-1H,5H-benzo[i,j]quinolizine-2-carboxylic acid.
57. 8-{4[(2S)-Amino-5-nitroguanidino-butanoyloxy]piperidin-1-yl}-9-fluoro-(5S)-methyl-6,7dihydro-1-oxo-1H,5H-benzo[i,j]quinolizine-2-carboxylic acid and hydrochloride.
58. 8-{4[(2S)-Amino-5-guanidino-butanoyloxy]piperidin-1-yl}-9-fluoro-(5S)-methyl-6,7dihydro-1-oxo-1H,5H-benzo[i,j]quinolizine-2-carboxylic acid.
59. 8-{4[(2S)-Amino-5-guanidino-butanoyloxy]piperidin-1-yl}-9-fluoro-(5S)-methyl-6,7dihydro-1-oxo-1H,5H-benzo[i,j]quinolizine-2-carboxylic acid and hydrochloride.
60. 8-{4[(2S)-Amino-5-nitroguanidino-butanoyl-(2S)-amino-5-nitroguanidino-butanoyloxy]piperidin-1-yl}-9-fluoro-(5S)-methyl-6,7dihydro-1-oxo-1H,5H-benzo[i,j]quinolizine-2-carboxylic acid.
61. 8-{4[(2S)-Amino-5-nitroguanidino-butanoyl-(2S)-amino-5-nitroguanidino-butanoyloxy]piperidin-1-yl}-9-fluoro-(5S)-methyl-6,7dihydro-1-oxo-1H,5H-benzo[i,j]quinolizine-2-carboxylic acid and hydrochloride.
62. 8-{4[(2S)-Amino-5-guanidino-butanoyl-(2S)-amino-5-guanidino-butanoyloxy]piperidin-1-yl}-9-fluoro-(5S)-methyl-6,7dihydro-1-oxo-1H,5H-benzo[i,j]quinolizine-2-carboxylic acid.
63. 8-{4[(2S)-Amino-5-guanidino-butanoyl-(2S)-amino-5-guanidino-butanoyloxy]piperidin-1-yl}-9-fluoro-(5S)-methyl-6,7dihydro-1-oxo-1H,5H-benzo[i,j]quinolizine-2-carboxylic acid and hydrochloride.

The hydrates of all the above compounds are also compounds of the invention. Hydrate may be represented by the term hydrate or $H_2O$.

One embodiment of the invention are the salts and hydrates of S-(−)-Nadifloxacin. Another embodiment of the invention are the derivatives and salts of the S-(−)-benzoquinolizine carboxylic acids of the invention which are essentially prodrugs of compounds of the formula I having free carboxylic acid groups or hydroxy groups. Prodrugs are understood to be esters of the free carboxylic acid group, or amides of the free carboxylic acid group with ammonia, organic amines or the amino group of an amino acid residue, or a polypeptide chain of two or more, such as up to four, amino acids residues which are covalently joined through peptide bonds. Prodrugs are also understood to be ethers of the free 4-OH group of the piperidinyl moiety or esters of the free 4-OH-group of the piperidinyl moiety with a carboxylic acid residue as defined for formula I above or with the carboxylic acid group of an organic acid, organic dibasic acid or an amino acid residue, or a polypeptide chain of two or more, such as up to four, amino acid residues which are covalently joined through peptide bonds. The amino acid residues of use include the 20 naturally occurring amino acids alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. Preferred amino acid residues are those with a basic-polar group such as Nitro-Arg, Arg, Lys, His, and those with a polar group such as Ala, Val, Nval, Leu, Met, Gly, Pro, Phe. Prodrugs at the free 4-OH group may also be phosphoric acid esters and sulfonic acid esters.

Particularly, the preferred compounds of the present invention are:

S-(−)-9-fluoro-6,7-dihydro-8-(4-hydroxypiperidin-1-yl)-5-methyl-1-oxo-1H,5H-benzo[i,j]quinolizine-2-carboxylic acid S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate S-(−)-9-fluoro-6,7-dihydro-8-(4-hydroxypiperidin-1-yl)-5-methyl-1-oxo-1H,5H-benzo[i,j]quinolizine-2-carboxylic acid sodium salt S-(−)-9-fluoro-6,7-dihydro-8-(4-hydroxypiperidin-1-yl)-5-methyl-1-oxo-1H,5H-benzo[i,j]quinolizine-2-carboxylic acid sodium salt monohydrate S-(−)-9-fluoro-6,7-dihydro-8-(4-hydroxypiperidin-1-yl)-5-methyl-1-oxo-1H,5H-benzo[i,j]quinolizine-2-carboxylic acid arginine salt 0.25 $H_2O$ S-(−)-9-fluoro-6,7-dihydro-8-(4-hydroxypiperidin-1-yl)-5-methyl-5-oxo-1H,5H-benzo[i,j]quinolizine-2-carboxylic acid arginine salt .0.75 $H_2O$ 8-{4-[2(S)-Amino-propionyloxy]piperidin-1-yl}-9-fluoro-5(S)-methyl-6,7-dihydro-1-oxo-1H,5H-benzo[i,j]quinolizine-2-carboxylic acid 8-{4-[2(S)-Amino-propionyloxy]piperidin-1-yl}-9-fluoro-5(S)-methyl-6,7-dihydro-1-oxo-1H,5H-benzo[i,j]quinolizine-2-carboxylic acid, hydrochloride 8-{4-[2(R)-Amino-propionyloxy]piperidin-1-yl}-9-fluoro-5(S)-methyl-6,7-dihydro-1-oxo-1H,5H-benzo[i,j]quinolizine-2-carboxylic acid acetate 8-{4[(2S)-Methylamino-propionyloxy]piperidin-1-yl}-9-fluoro-(5S)-methyl-6,7dihydro-1-oxo-1H,5H-benzo[i,j]quinolizine-2-carboxylic acid 8-{4[(2S)-Methylamino-propionyloxy]piperidin-1-yl}-9-fluoro-(5S)-methyl-6,7dihydro-1-oxo-1H,5H-benzo[i,j]quinolizine-2-carboxylic acid, hydrochloride Even more preferred compounds of the invention are:

S-(−)-9-fluoro-6,7-dihydro-8(-4-hydroxypiperidin-1-yl)-5-methyl-1-oxo-1H,5H-benzo[i,j]quinolizine-2-carboxylic acid 0.2 hydrate.

S-(−)-9-fluoro-6,7-dihydro-8(-4-hydroxypiperidin-1-yl)-5-methyl-1-oxo-1H,5H-benzo[i,j]quinolizine-2-carboxylic acid sodium salt monohydrate.

8-{4-[2(R)-Amino-propionyloxy]piperidin-1-yl}-9-fluoro-5(S)-methyl-6,7-dihydro-1-oxo-1H,5H-benzo[i,j]quinolizine-2-carboxylic acid, acetate.

8-{4-[2(S)-Amino-propionyloxy]piperidin-1-yl}-9-fluoro-5(S)-methyl-6,7-dihydro-1-oxo-1H,5H-benzo[i,j]quinolizine-2-carboxylic acid, hydrochloride.

S-(−)-9-fluoro-6,7-dihydro-8-(4-hydroxypiperidin-1-yl)-5-methyl-1-oxo-1H,5H-benzo[i,j]quinolizine-2-carboxylic acid arginine salt 0.25 $H_2O$.

S-(−)-9-fluoro-6,7-dihydro-8-(4-hydroxypiperidin-1-yl)-5-methyl-1-oxo-1H,5H-benzo[i,j]quinolizine-2-carboxylic acid arginine salt 0.75 $H_2O$.

Even more preferred compounds of the invention are S-(−)-9-fluoro-6,7-dihydro-8-(4-hydroxypiperidin-1-yl)-5-methyl-1-oxo-1H,5H-benzo[i,j]quinolizine-2-carboxylic acid arginine salt 0.25 $H_2O$ and S-(−)-9-fluoro-6,7-dihydro-(8-4-hydroxypiperidin-1-yl)-5-methyl-1-oxo-1H,5H-benzo[i,j]quinolizine-2-carboxylic acid arginine salt .0.75 $H_2O$.

In addition to their favorable aqueous solubility, the respective arginine salts on repeated i.v. administration in rats did not cause phlebitis at doses double those of the corresponding sodium salt. This feature would make S-(−)-9-fluoro-6,7-dihydro-8-(4-hydroxypiperidin-1-yl)-5-methyl-1-oxo-1H,5H-benzo[i,j]quinolizine-2-carboxylic acid arginine salt 0.25 $H_2O$ and S-(−)-9-fluoro-6,7-dihydro-8-[4-(hydroxy)-1-piperidin-1-yl)-5-methyl-1-oxo-1H,5H-benzo[i,j]quinolizine-2-carboxylic acid arginine salt 0.75 $H_2O$ suitable for long term i.v. administration which is commonly undertaken for critically ill patients or patients in intensive care unit.

The compounds, derivatives, salts, pseudopolymorphs, polymorphs and hydrates of the invention as defined above exhibit the same potent antibacterial activity as S-(−)-Nadifloxacin and also have one or more desirable physico-chemical properties such as constant moisture content, excellent solubility etc. regardless of the ambient relative humidity, and also have desirable bioavailability and safety profiles.

Generally, conversion of a pharmacologically active compound into a salt or hydrate form induces a change in the compound's physicochemical properties such as solubility, absorption velocity, etc. Therefore, study about an effective salt or hydrate form for developing a successful new medicine has been conventionally made. Pharmaceutically more desirable crystal form may be selected by studying whether or not any polymorphs or pseudopolymorph can be produced and its physicochemical properties (see, Remington's Pharmaceutics, Chapter 75 Preformulation; Byrn, S. R. Solid Chemistry of Drugs, Academic Press, New York, 1982). The hydrate, one such polymorph or pseudopolymorph, has water molecules inside the crystal, and thus has a crystalline structure different from that of the anhydrate, as can be verified from their respective X-ray diffraction patterns. A polymorph or pseudopolymorph differs from the original compound not in its chemical properties, such as pharmacological activity, but in its physical properties, such as crystallinity, hygroscopicity, melting point, solubility, solubilizing velocity, etc. So, the polymorph or pseudopolymorph has been recognized as pharmaceutically important (see, Morris, K. P. et. al. Int. J. Pharm., 108, 15-206 (1994)). In the process of identifying the physico-chemical properties of S-(−)-Nadifloxacin, the compound has been found to exist as a stable hydrate wherein the proportion of water molecules contained in one molecule varies within a specific range. Here, stability does not mean chemical stability but the difficulty of removing water molecules. That is, a stable hydrate neither loses the water molecule contained therein, nor absorbs moisture over a wide range of ambient relative humidity. In contrast, moisture absorption by the anhydrate can vary greatly with the ambient relative humidity. As a result of experiments carried out by the present inventors, S-(−)-9-fluoro-6,7-dihydro-8-(4-hydroxypiperidin-1-yl)-5-methyl-1-oxo-1H,5H-benzo[i,j]quinolizine-2-carboxylic acid has been shown to exist as a stable hydrate for values of the hydration number z equal to 0.2, 0.5 or 0.75. In addition to the anhydrate S-(−)-Nadifloxacin, the inventors have now found that S-(−)-9-fluoro-6,7-dihydro-8-(4-hydroxypiperidin-1-yl)-5-methyl-1-oxo-1H,5H-benzo[i,j]quinolizine-2-carboxylic acid may exist as a 0.2 hydrate, 0.5 hydrate and 0.75 hydrate crystal forms. Among these, 0.2 is preferred since the change in moisture content is the lowest at the hydration number. Although stable hemihydrate and the hemisesquihydrate forms can be prepared, they alter also to the 0.2 hydrate on vacuum drying at room temperature.

The moisture content of the hydrate varies with the hydration number (z) of the hydrated molecule. The actual moisture content may however, differ from the calculated moisture content depending on differences in recrystallization conditions, drying conditions, etc. The range of the actual moisture content for the 0.2 hydrate is from 0.9% to 1.1%, even though the calculated moisture content is 0.99%.

It has also been found that the relative humidity range at which the moisture content of the anhydrate and the 0.2 hydrate can be maintained constant differ from each other. That is, although the anhydrate has a constant moisture content at a relative humidity of 20% to 75%, the 0.2 hydrate is constant at a relative humidity of 20% to 95% (see FIGS. 1 and 2).

The hydrates of formula I may be prepared by means of conventional methods well known in the art to which the present invention pertains. Particularly, the different hydrates may be prepared merely by changing recrystallization conditions, and the temperature/vacuum conditions under which the crystals are dried. The 0.2 hydrate is prepared by dissolving S-(−)-9-fluoro-8(4-hydroxypiperidin-1-yl)-5-methyl-6,7-dihydro-1-oxo-1H,5H-benzo[i,j]quinolizine-2-carboxylic acid in a minimum volume of organic solvent, preferably acetonitrile or ethanol at an elevated temperature, preferably at the reflux temperature of the solvent and adding an amount of water sufficient to bring about crystallisation after cooling in high yields, filtering and drying the separated crystals at temperatures up to 40-50° C. for 3-6 hours, preferably 5 hours, in vacuo upto 50 mm of Hg to a constant weight. The 0.2 hydrate can also be prepared by dissolving S-(−)-9-fluoro-8-(4-hydroxypiperidin-1-yl)-5-methyl-6,7-dihydro-1-oxo-1H,5H-benzo[i,j]quinolizine-2-carboxylic acid in alkali, preferably 1 molar aqueous sodium hydroxide, heating to 55-60° C., acidifying, preferably with concentrated hydrochloric acid, at 55-60° C., maintaining the suspension at 50-70° C., preferably at 60° C. for at least 30 minutes, cooling, filtering, washing with water and drying the separated crystals at temperatures up to 40-50° C. for 3-6 hours, preferably 5 hours, in vacuo upto 50 mm of Hg to a constant weight.

The 0.5 hydrate can be prepared by dissolving S-(−)-9-fluoro-8-(4-hydroxypiperidin-1-yl)-5-methyl-6,7-dihydro-1-oxo-1H,5H-benzo[i,j]quinolizine-2-carboxylic acid in an minimum volume of organic solvent such as acetone at reflux temperature adding an appropriate amount of water at ambient temperature, sufficient to bring about crystallisation after cooling in high yields, filtering and drying the separated crystals at temperatures up to <40° C. for 3-6 hours, preferably 5 hours to a constant weight.

The 0.75 hydrate can be prepared by suspending S-(−)-9-fluoro-8(4-hydroxypiperidin-1-yl)-5-methyl-6,7-dihydro-1-oxo-1H,5H-benzo[i,j]quinolizine-2-carboxylic acid in water, preferably at 10% (weight by volume) suspension, formulating into a slurry by vigorous stirring continuing stirring at 5° C. for 1-2 hours, adding acetone ca. 5% (weight by volume) with continuation of stirring at 5° C. for 4-5 hours, filtering and drying the product at temperatures <40° C. for 3-6 hours, preferably 5 hours, to a constant weight.

The methods as stated above will be more specifically explained in the examples described in appropriate later section of this text.

The novel compounds of the Formula I with pharmaceutically acceptable cations are prepared by reacting an appropriate benzoquinolizine carboxylic acid, for example, S-(−)-nadifloxacin with a base capable of releasing the cation X, wherein X is as defined in $OR_1$ above to give the desired salt of Formula I. Examples of bases capable of releasing the cation X and examples of reaction conditions are given below.

a) Salts of the formula I, wherein the cation $R_1$ is lithium, sodium or potassium are prepared by treating a compound of the formula I wherein X═OH with LiOH, NaOH, $NaHCO_3$, $Na_2CO_3$, KOH, $KHCO_3$ or $K_2CO_3$ in an aqueous or non-aqueous medium.

b) Salts of the formula I, wherein the cation $R_1$ is magnesium, or calcium, are prepared by treating a compound of the formula I wherein X═OH with $Mg(OH)_2$, or $Ca(OH)_2$, in an aqueous or non-aqueous medium.

c) Salts of the formula I, wherein the cation $R_1$ is a basic compound like a basic amino acid or an organic basic amine are prepared by treating a compound of the formula I, wherein X═OH with an aqueous or alcoholic solution of the appropriate basic amino acid or organic basic amine.

d) The compound I of the invention which are esters at the carboxylic acid group may be prepared by treating the free acid compound I in solution in an appropriate solvent, preferably N,N-dimethyl formamide, with the corresponding halo compound, preferably chloro or bromo-compound, in the presence of a base, preferably anhydrous potassium carbonate, at an elevated temperature, preferably 50° C. for an extended period of time, preferably 6 hours.

e) The compounds I of the invention which are amides at the carboxylic acid groups may be prepared by coupling the free acid compound I with ammonia or an appropriate amine or an amino acid appropriately protected at the acid functionality of the amino acids with a protecting group. The —COOH protecting groups for amino acids are known in the art. Examples of suitable —COOH protecting groups for amino acids are methyl, ethyl, t-butyl and benzyl groups. The —COOH protecting group is removed by hydrolysis or by hydrogenation. The coupling of the —COOH group of compound I with the amino group of the amino acid is also known in the art. The reaction may be conducted with or without a solvent at a range of temperatures in the presence of a coupling agent.

f) The compounds I of the invention which are ethers at the 4-OH group may be conveniently prepared by condensing the previously prepared 4-alkoxypiperidine with S-(−)-diacetoxy-(8,9-difluoro-6,7-dihydro-1-oxo-1H,5H-benzo[i,j]quinolizine-2-carboxyl)borane. The reaction may be conducted with or without a solvent at a range of temperatures in the presence of a condensing agent.

g) The compounds of the invention which are esters at the 4-OH group may be prepared by treating the free 4-OH compound I with an organic acid, an organic dibasic acid or appropriate N-protected amino acid or polypeptide as defined above. Nitrogen protecting groups are known in the art. Examples of suitable nitrogen protecting groups are $C_1$-$C_6$ acyl, $C_2$-$C_6$ alkoxycarbonyl optionally substituted benzyloxycarbonyl, aryloxycarbonyl, silyl, trityl, tetrahydropyranyl, vinyloxycarbonyl, O-nitrophenylsulfonyl, diphenylphosphinyl, p-toluenesulfonyl, and benzyl. The nitrogen protecting group is removed by methods known in the art such as hydrogenation or hydrolysis. The ester forming reaction may be conducted with or without a solvent at a range of temperatures in the presence of a suitable condensing agent, known to those skilled in the art.

h) The pharmaceutically acceptable acid addition salts of compounds I are prepared in a conventional manner by treating a solution or suspension of the free base I with about one chemical equivalent of a pharmaceutically acceptable acid. Conventional concentration and recrystallization techniques are employed in isolating the salts. Illustrative of suitable acids are acetic, lactic, oxalic, succinic, maleic, tartaric, citric, gluconic, ascorbic, benzoic, methanesulfonic, p-toluenesulfonic, cinnamic, fumaric, phosphoric, hydrochloric, hydrobromic, hydroiodic, sulfamic, and sulfonic acid.

i) The pharmaceutically acceptable cationic salts of compounds I may be prepared by conventional methods from the corresponding acids e.g. by reaction with about one equimolar amount of a base. Examples of suitable cationic salts are those of alkali metals such as sodium or potassium, alkaline earth metals such as magnesium or calcium and ammonium or organic amines such as diethanolamine or N-methylglucamine.

The present invention encompasses a method of treating bacterial infections, especially resistant Gram-positive organism infections, Gram-negative organism infections, mycobacterial infections and nosocomial pathogen infections in humans and animals, which comprises administering systemically or topically to a human or animal in need of such antiinfective therapy an amount of S-(−)-Nadifloxacin or an optically pure benzoquinolizine carboxylic acid, their derivatives, salts, pseudopolymorphs, polymorphs and hydrates thereof, of the formula I as defined above, substantially free of its R-(+)-enantiomer, said amount being sufficient to eradicate such infections. The method avoids the concomitant liability of toxic effects associated with the administration of RS-(±)-isomers by providing an amount of S-(−)-Nadifloxacin or an optically pure benzoquinolizine carboxylic acid, their derivatives, salts, pseudopolymorphs, polymorphs and hydrates thereof, of the invention, which is insufficient to cause the toxic effects associated with the racemic mixture of the isomers.

The present invention also encompasses an antiinfective composition for the treatment of humans and animals in need of therapy for systemic or topical infections especially resistant Gram-positive organism infections, Gram-negative organism infections, mycobacterial infections and nosocomial pathogen infections, which comprises an amount of S-(−)-Nadifloxacin and optically pure benzoquinolizine carboxylic acids, the derivatives, salts, pseudopolymorphs, polymorphs and hydrates thereof, of Formula I as defined above, substantially free of their R-(+)-enantiomers, said amount being sufficient to eradicate said infection. The composition should provide a therapeutic dose, which is insufficient to cause the toxic effects associated with the comparable compositions comprised of racemic RS-(±)-isomeric mixture.

S-(−)-Nadifloxacin and the compounds of the invention have 2-4 times higher antimicrobial activity than RS-(±)-Nadifloxacin against Mupirocin-resistant staphylococci, Methicillin-resistant *Staphylococcus aureus* (MRSA), Quinolone-resistant *Staphylococcus aureus*, coagulase negative staphylococci, such as Methicillin-resistant *Staphylococcus epidermidis* (MRSE), enterococci, betahemolytic streptococci and viridans group of streptococci. The antimicrobial profile of S-(−)-Nadifloxacin and the compounds of the invention have, thus, a potential to address several unmet antibacterial treatment needs ascribed to the most frequently encountered Gram-positive bacterial pathogens in clinical settings. S-(−)-Nadifloxacin and the compounds of the invention possesses superior antibacterial activity against such Gram-positive pathogens which have now become refractory to older first- and second-line antibacterials mentioned above (cf. Biological Example 1). Infections such as impetigo, pneumonia, bronchitis, pharyngitis, endocarditis, urinary tract infections and bacteremias caused by *Staphylococcus aureus*, coagulase negative staphylococci, enterococci, beta haemolytic streptococci and viridans group of streptococci are potentially amenable to successful treatment with S-(−)-Nadifloxacin and the compounds of the invention. Intrinsically high potency of S-(−)-Nadifloxacin and the compounds of the invention coupled with their powerful bactericidal action against organisms such as *S. aureus*, Coagulase negative staphylococci and enterococci renders S-(−)-Nadifloxacin and the compounds of the invention eminently suitable for the treatment of infections caused by multi-drug resistant strains belonging to this group.

There is a surge of mycobacterial infections due to the spread of AIDS such as in several countries of Europe, USA and Asia. AIDS and other immunocompromised patients frequently contract mycobacterial infections due to multi-drug resistant *M. tuberculosis* and other atypical mycobacteria such as *M. intracellulare* and *M. avium*. An embodiment of this invention is that the antimycobacterial profile of S-(−)-Nadifloxacin and the compounds of the invention have been found to display significant activity against such organisms and provide a valuable option for the treatment of such problematic diseases. In addition, S-(−)-Nadifloxacin and the compounds of the invention have been shown by the present inventors to display negligible phototoxicity potential than the comparator fluoroquinolone drug sparfloxacin. In studies conducted by the present inventors Sparfloxacin was found to be phototoxic at dosages 25 times lower than S-(−)-Nadifloxacin and the compounds of the invention.

S-(−)-Nadifloxacin and the compounds of the invention also possesses high level of activity against newly emerging Gram-negative pathogens such as *Chryseobacterium meningosepticum* and *Chryseobacterium indologense*. These organisms frequently infect immunocompromised adults as well as premature neonats. These organisms are nosocomial pathogens against which most of the currently available antibacterial agents possess either poor or only borderline activity. The present investigations have shown that S-(−)-Nadifloxacin and the compounds of the invention in possessing superior activity against chryseobacteria and other nosocomial pathogens such as MRSA, enterococci and methicillin susceptible strains of staphylococci have a potential to become excellent drugs for the treatment of hospital acquired infections (cf. Biological Example 1).

Against bacterial organisms which proliferate in acidic environment such as the urinary tract, S-(−)-Nadifloxacin and the compounds of the invention behave in a characteristically different pattern than do the known fluoroquinolones, such as Ciprofloxacin, Levofloxacin, Ofloxacin and Norfloxacin. In studies carried out by the present inventors the antibacterial potency, that is MIC value, as well as bactericidal action of S-(−)-Nadifloxacin against Gram-positive pathogens such as staphylococci and enterococci, and Gram-negative pathogens such as *E. coli, Klebsiella, Proteus, Serratia, Citrobacter*, and *Pseudomonas*, unlike that of Ciprofloxacin and Levofloxacin, is not affected at all by the acidic pH of 5.5. On the contrary, for some organisms the MIC of S-(−)-Nadifloxacin improves by 100% while that for Ciprofloxacin and Levofloxacin deteriorates in the range of from 50% to 99% (Biological Example 2). Further confirmation of these results were obtained by comparatively evaluating the antibacterial activity of S-(−)-Nadifloxacin, Ciprofloxacin and Levofloxacin in normal human urine against a range of organisms frequently encountered in urinary tract infections. For Ciprofloxacin and Levofloxacin the loss in antibacterial activity coupled with the abolition of bactericidal action occurring at acidic pH would lead to recurrent episodes of urinary tract infections in patients receiving such fluoroquinolone antibacterial drugs, whereas treatment with S-(−)-Nadifloxacin and the compounds of the invention, would lead to successful and consistent cure, irrespective of the pH or the nature of the environment in which bacterial pathogens are proliferating. This unpredictable finding with S-(−)-Nadifloxacin is of great clinical relevance and would provide a unique advantage to patients on a regimen of the compounds of the invention for urinary tract infections.

In gram-positive bacteria, especially *Staphylococcus* strains, resistance to most of the fluoroquinolones in clinical use is mediated by the presence of efflux pumps, in particular Nor A efflux pumps, which affects the accumulation of the antibiotics within the cell by enhancing efflux, thus preventing the antibiotic action. Current estimates of prevalence of Nor A bearing strains among ciprofloxacin resistant staphylococci is about 30-80%.

The present inventors have surprisingly and unexpectedly found that in studies with fluoroquinolone-resistant *Staphylococcus* strains with efflux pumps, while most of the fluoroquinolones in current clinical use have shown significantly reduced potency against the efflux-pump bearing *Staphylococcus* strains, S-(−)-Nadifloxacin, its hydrates, salts, pseudopolymorphs, polymorphs and derivatives thereof, have shown no loss in potency of activity in both in-vitro and in-vivo conditions (Biological Examples 6 & 7). These results support the reduced effectiveness of the current fluoroquinolones in clinical use in treating infections caused by such efflux-pump-bearing staphylococcal strains. These results, thus, create a novel opportunity for clinical use of the compounds of the invention in treating infections caused by efflux-pump bearing strains, in particular efflux-pump bearing *Staphylococcal* strains.

The finding of this property of the compounds of the invention is not suggested by the prior art. In thus behaving differently from the general class of fluoroquinolones, S-(−)-Nadifloxacin and the compounds of the invention display a property hitherto not yet shown. It has arisen because of the in-depth studies undertaken by the inventors of the compounds of the invention, without any reasonable expectation of the kind of result that has been obtained.

The high propensity of S-(−)-Nadifloxacin to display resistance to resistance development in comparison to current fluoroquinolone drugs in clinical use has also now been shown for the first time by the inventors. In studies, which mimic the clinical scenario, S-(−)-Nadifloxacin was evaluated in comparison with trovafloxacin and gatifloxacin by sequential transfer/passages through respective drug containing media. Although initially all the three drugs had comparable activity against *S. aureus* strain 042, after six passages in drug containing media, whilst S-(−)-Nadifloxacin showed a marginal rise of 4% in MIC value, trovafloxacin and gatifloxacin showed approximately 300% and 700% rise respectively in MIC values. This property of S-(−)-Nadifloxacin to display resistance to resistance development has considerable value clinically. In clinical settings, the ability of pathogenic bacteria to select a drug resistant variant/subclone while the patient is on antibacterial drug therapy often determines the outcome of the therapy. A drug to which such resistant variant comes up readily, often witnesses failure of therapy, or a need to increase the dosage significantly, thereby dramatically increasing the chances of exposing patients to adverse side effects also.

These combined features of S-(−)-Nadifloxacin and optically pure benzoquinolizine carboxylic acids, the derivatives, salts, pseudopolymorphs, polymorphs and hydrates thereof of activity against bacterial organisms which proliferate in acidic environment, of an ability to resist the action of efflux pump present in drug resistant microbial strains and of a propensity to display resistance to resistance development, endows the compounds of the invention with a unique clinical potential yet not realized in other fluoroquinolone antibacterials in current medical use.

The above list of pathogens is merely by way of example and is in no way to be interpreted as limiting. Examples which may be mentioned of diseases, which can be prevented, alleviated and/or cured by the formulations according to the invention are otitis externa, otitis media; pharyngitis; pneumonia; peritonitis; pyelonephritis; cystitis; endocarditis; systemic infections; bronchitis; arthritis; local infections; and septic diseases.

These findings have an important implication from the point of view of the systemic use of S-(−)-Nadifloxacin and the compounds of the invention, which in view of their superior potency, superior bactericidal activity, expanded biospectrum, better bioavailability and improved tolerability are now enabled to be administered systemically in doses that are insufficient to cause the toxic effects associated with the administration of racemic RS-(±)-Nadifloxacin and corresponding racemic mixtures of compounds of the invention.

Utilizing the substantially optically pure or optically pure isomer of Nadifloxacin or optically pure benzoquinolizine carboxylic acids, the derivatives, salts, hydrates, pseudopolymorphs, or polymorphs thereof, whether in systemic or topical dosage form, results in clearer dose-related definitions of efficacy, diminished toxic effects and accordingly an improved therapeutic index. It is, therefore, more desirable to administer the S-(−)-isomer of Nadifloxacin and S-(−)-optically pure benzoquinolizine carboxylic acid, their derivatives, salts, pseudopolymorphs, polymorphs and hydrates thereof, than RS-(±)-Nadifloxacin and racemic mixtures of compounds of the invention.

The term "substantially free of its R-(+)-enantiomer" as used herein means that the compositions contain a greater proportion of the S-isomer of Nadifloxacin or an optically pure benzoquinolizine carboxylic acid, their derivatives, salts, pseudopolymorphs, polymorphs and hydrates thereof, in relation to the R-isomer. In a preferred embodiment, the term "substantially free of its R-isomer" as used herein means that the composition is at least 90% by weight of S-(−)-Nadifloxacin or an optically pure benzoquinolizine carboxylic acid, their derivatives, salts, pseudopolymorphs, polymorphs and hydrates thereof, and 10% by weight or less of the corresponding R-(+)-isomer. In a more preferred embodiment the term "substantially free of the R-enantiomer" means that the composition is at least 99% by weight of S-(−)-Nadifloxacin or an optically pure benzoquinolizine carboxylic acid, their derivatives, salts, pseudopolymorphs, polymorphs and hydrates thereof, and 1% by weight or less of the corresponding R-(+)-isomer. In the most preferred embodiment the term "substantially free of the R-enantiomer" means that the composition contains greater than 99% by weight of S-(−)-Nadifloxacin or an optically pure benzoquinolizine carboxylic acid, their derivatives, salts, pseudopolymorphs, polymorphs and hydrates thereof. These percentages are based on the total amount of Nadifloxacin in the composition. The terms "substantially optically pure S-isomer of Nadifloxacin or an optically pure benzoquinolizine carboxylic acid, their derivatives, salts, pseudopolymorphs, polymorphs and hydrates thereof" or "substantially optically pure S-Nadifloxacin or an optically pure benzoquinolizine carboxylic acid, their derivatives, salts, pseudopolymorphs, polymorphs and hydrates thereof" and "optically pure S-enantiomer of Nadifloxacin or an optically pure benzoquinolizine carboxylic acid, their derivatives, salts, pseudopolymorphs, polymorphs and hydrates thereof" or "optically pure S-Nadifloxacin or an optically pure benzoquinolizine carboxylic acid, their derivatives, salts, pseudopolymorphs, polymorphs and hydrates thereof" are also encompassed by the above described amounts.

The pharmaceutical compositions are prepared according to conventional procedures used by persons skilled in the art to make stable and effective compositions. In the solid, liquid, parenteral and topical dosage forms, an effective amount of the active compound or the active ingredient is any amount, which produces the desired results.

For the purpose of this invention the pharmaceutical compositions may contain the active compounds, S-(−)-Nadifloxacin or an optically pure benzoquinolizine carboxylic acid, their derivatives, salts, pseudopolymorphs, polymorphs and hydrates thereof, in a form to be administered alone, but generally in a form to be administered in admixture with a pharmaceutical carrier selected with regard to the intended route of administration and standard pharmaceutical practice. Suitable carriers which can be used are, for example, diluents or excipients such as fillers, extenders, binders, emollients, wetting agents, disintegrants, surface active agents, humectants, antioxidants, sequestering agents and lubricants which are usually employed to prepare such drugs depending on the type of dosage form.

Any suitable route of administration may be employed for providing the patient with an effective dosage of S-(−)-Nadifloxacin or an optically pure benzoquinolizine carboxylic acid, their derivatives, salts, pseudopolymorphs, polymorphs and hydrates thereof. For example, oral, rectal, parenteral (subcutaneous, intramuscular, intravenous), transdermal, topical and like forms of administration may be employed. Dosage forms include (solutions, suspensions, etc) tablets, pills, powders, troches, dispersions, suspensions, emulsions, solutions, capsules, injectable preparations, patches, ointments, creams, lotions, gels, sprays, shampoos and the like.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

The compositions of the present invention include compositions such as suspensions, solutions, elixirs, aerosols, and solid dosage forms. Carriers as described in general above are commonly used in the case of oral solid preparations (such as powders, capsules and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. Examples of suitable carriers include excipients such as lactose, white sugar, sodium chloride, glucose solution, urea, starch, calcium carbonate, kaolin, crystalline cellulose and silicic acid, binders such as water, ethanol, prepanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic acid salts, boric acid powder, polyethylene glycol and solid polyethylene glycol.

The tablet, if desired, can be coated, and made into sugar-coated tablets, gelatin-coated tablets, enteric-coated tablets, film-coated tablets, or tablets comprising two or more layers.

If desired, tablets may be coated by standard aqueous or nonaqueous techniques.

Desirably, each tablet, cachet, capsule contains from about 200 mg to about 1500 mg of the active ingredient. Most preferably, the tablet, cachet or capsule contains either one of three dosages, about 200 mg, about 400 mg, or about 600 mg of the active ingredient.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar.

In molding the pharmaceutical composition into a suppository form, a wide variety of carriers known in the art can be used. Examples of suitable carriers include polyethylene glycol, cacao butter, higher alcohols, gelatin, and semi-synthetic glycerides.

A second preferred method is parenterally for intramuscular, intravenous or subcutaneous administration.

A third preferred route of administration is topically, for which creams, ointments, sprays, shampoos, lotions, gels, dusting powders and the like are well suited. Generally, an effective amount of the compound according to this invention in a topical form is 0.1% to about 10% by weight of the total composition. Preferably, the effective amount is 1% by weight of the total composition.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient preferably in combination with a solid or liquid inert carrier material.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

The antimicrobial pharmaceutical composition may further contain ordinary dissolving aids, buffers, pain-alleviating agents, and preservatives, and optionally coloring agents, perfumes, flavors, sweeteners, and other drugs.

A specific embodiment of the invention is the preparation of storage stable compositions of the compounds of the invention of formula I. Such stable compositions can be advantageously made through the use of selective stabilizers. Different stabilizers are known to those skilled in the art of making pharmaceutical compositions. Of special utility for making storage stable compositions of the compound of the invention of formula I, stabilizers such as disodium EDTA, tromethamine, cyclodextrins such as gamma-cyclodextrin, beta-cyclodextrin, hydroxy-propyl-gamma-cyclodextrin have been found to be useful.

A specific embodiment of the invention utilizes arginine as an excipient in compositions to facilitate the aqueous solubility of the compounds of the invention which comprises utilizing an appropriate molar amount of arginine with a specific compound of the invention. For example, a 0.7 molar amount of arginine added to a molar amount of S-(−)-9-fluoro-8-(4-hydroxypiperidin-1-yl)-5-methyl-6,7-dihydro-1-oxo-1H,5Hbenzo[i,j]quinolizine-2-carboxylic acid arginine salt 0.75 $H_2O$, raises the aqueous solubility of the salt from 94 mg/ml to a value >200 mg/ml.

In a specific embodiment of the invention, the pharmaceutical compositions contain an effective amount of the active compounds of S-(−)-9-fluoro-8-(4-hydroxypiperidin-1-yl)-5-methyl-6,7-dihydro-1-oxo-1H,5H benzo[i,j]quinolizine-2-carboxylic acid (also called S-(−)-Nadifloxacin) or one of the specific optically pure derivatives, salts, pseudopolymorphs, polymorphs or hydrates thereof described in this specification in admixture with a pharmaceutically acceptable carrier, diluent or excipients, and optionally other therapeutic ingredients.

The prophylactic or therapeutic dose of S-(−)-Nadifloxacin and optically pure benzoquinolizine carboxylic acids, the derivatives, salts, pseudopolymorphs, polymorphs or hydrates thereof, in the acute or chronic management of disease will be calculated based on the prophylactic or therapeutic dose of S-(−)-9-fluoro-8-(4-hydroxypiperidin-1-yl)-5-methyl-6,7dihydro-1-oxo-1H,5H benzo[i,j]quinolizine-2-carboxylic acid and will vary with the severity of condition to be treated, and the route of administration. In addition, the dose, and perhaps the dose frequency, will also vary according to the age, body weight and response of the individual patient. In general, the total daily dose range, for S-(−)-Nadifloxacin or an optically pure benzoquinolizine carboxylic acids, the derivatives, salts, pseudopolymorphs, polymorphs or hydrates thereof, for the conditions described herein, is from about 200 mg to about 1500 mg, in single or divided doses. Preferably, a daily dose range should be between about 400 mg to 1200 mg, in single or divided dosage, while most preferably a daily dose range should be between about 500 mg to about 1000 mg in divided dosage. While intramuscular administration may be a single dose or upto 3 divided doses, intravenous administration can include a continuous drip. It may be necessary to use dosages outside these ranges in some cases as will be apparent to those skilled in the art. Further, it is noted that the clinician or treating physician will know how and when to interrupt, adjust, or terminate therapy in conjunction with individual patient's response. The term "an amount sufficient to eradicate such infections but insufficient to cause said toxic effect" is encompassed by the above-described dosage amount and dose frequency schedule.

The invention is further defined by reference to the following examples describing in detail the preparation of the composition of the present invention as well as their utility. It will be apparent to those skilled in the art that many modifications, both to materials and methods may be practiced without departing from the purpose and scope of this invention.

The following examples illustrate the methods of preparation of the compounds of the invention and are provided only as examples, but not to limit the scope of the compounds of the invention.

Example 1

S-(−)-9-fluoro-6,7-dihydro-8-(4-hydroxypiperidin-1-yl)-5-methyl-1-oxo-1H,5H-benzo[i,j]quinolizine-2-carboxylic acid anhydrate Method A S-(−)-9-fluoro-6,7-dihydro-8-(4-hydroxypiperidin-1-yl)-5-methyl-1-oxo-1H,5H-benzo[i,j]quinolizine-2-carboxylic acid (3.0 g) obtained according to the process described in literature [K. Hashimoto et. al., Chem. Pharm. Bull. 44, 642-5(1996)] was dissolved in acetonitrile (250 ml) at 85° C. The resulting clear solution was filtered (to remove if any fibrous material is in suspension). The filtrate was concentrated to 125 ml and left at room temperature for crystallization. The crystals thus separated were filtered and dried in a drying cabinet at 40° C. for 2 hr in vacuum at 50 mm of Hg to obtain constant weight. Yield 2.6 g (86%).

Method B:

S-(−)-9-fluoro-6,7-dihydro-8-(4-hydroxypiperidin-1-yl)-5-methyl-1-oxo-1H,5H-benzo[i,j]quinolizine-2-carboxylic acid (2.0 g) obtained according to the process described in literature [K. Hashimoto et. al., Chem. Pharm. Bull. 44, 642-5(1996)] was dissolved in ethyl alcohol (95%; 200 ml) at 80° C. The obtained clear solution was filtered (to remove if any fibrous material is in suspension), concentrated to 100 ml and left for crystallization. The separated solid was filtered and dried in a drying cabinet at 40° C. for 3 hr in vacuum at 50 mm of Hg to obtain constant weight. Yield 1.7 g (85%).

M.p.258-62° C., moisture content 0% (by Karl Fisher method) $[\alpha]_D^{26}$ −299°, HPLC purity 99.8%

Figure 3:
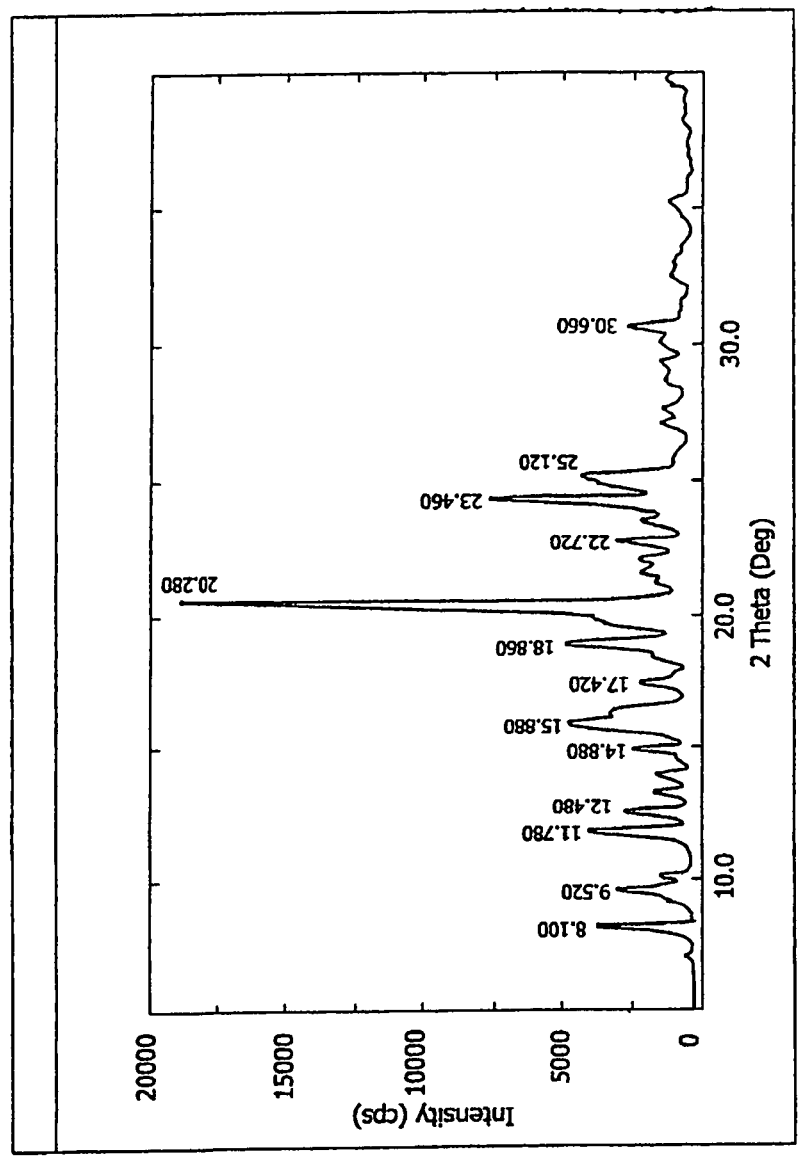
FIG. 3 represents the X-ray diffraction pattern of S-(−)-9-fluoro-6,7-dihydro-8-(4-hydroxypiperidin-1-yl)-5-methyl-1-oxo-1H,5H-benzo[i,j]quinolizine-2-carboxylic acid anhydrate.
4.
Figure 7:
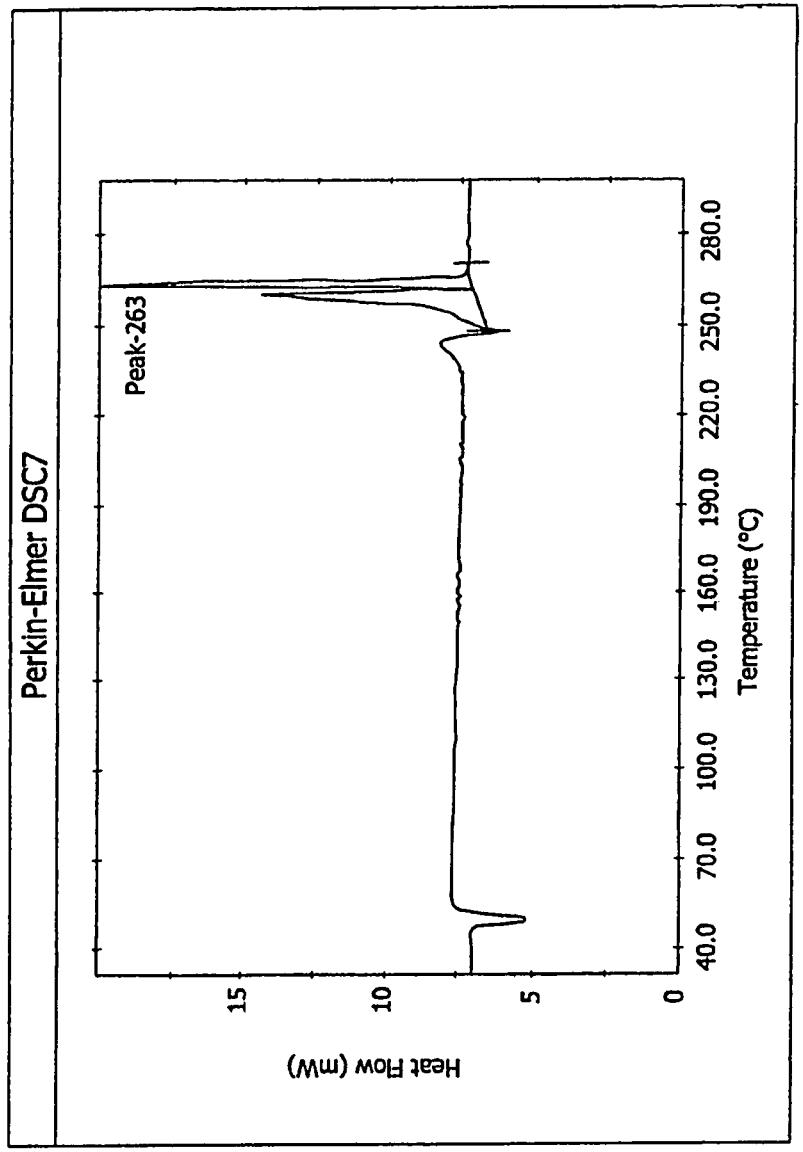
FIG. 7 represents the results of Differential Scanning Calorimetry on S-(−)-9-fluoro-6,7-dihydro-8-(4-hydroxypiperidin-1-yl)-5-methyl-1-oxo-1H,5H-benzo[i,j]quinolizine-2-carboxylic acid anhydrate
8.

The X-ray diffraction pattern and the DSC analysis of the sample were identical to that of the anhydrate shown in FIG. 3 and FIG. 7 respectively.

Example 2

S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate Method A:

S-(−)-9-fluoro-6,7-dihydro-8-(4-hydroxypiperidin-1-yl)-5-methyl-1-oxo-1H,5H-benzo[i,j]quinolizine-2-carboxylic acid (5.0 g) was dissolved in acetonitrile (500 ml) at 100° C. and filtered to remove suspended fibrous impurities. Distilled water (1500 ml) was added. On standing overnight at 5° C., the solid separated was filtered and dried at <50° C. for 5 hrs in vacuum at 50 mm of Hg to obtain constant weight. Yield 3.5 g (70%).

Method B:

S-(−)-9-fluoro-6,7-dihydro-8-(4-hydroxypiperidin-1-yl)-5-methyl-1-oxo-1H,5H-benzo[i,j]quinolizine-2-carboxylic acid (4.0 g) was dissolved in ethyl alcohol (200 ml) at 85° C. to obtain clear solution and distilled water (700 ml) was added. On standing overnight at 5° C., the solid thus separated was filtered and dried at <50° C. for 5 hrs in vacuum at 50 mm of Hg to obtain constant weight. Yield 3.1 g (77%).

Method C:

S-(−)-9-fluoro-6,7-dihydro-8-(4-hydroxypiperidin-1-yl)-5-methyl-1-oxo-1H,5H-benzo[i,j]quinolizine-2-carboxylic acid (1.0 g) was dissolved in aqueous NaOH (1M, 10 ml) with stirring at room temperature, and filtered to remove suspended fibrous impurities. The obtained clear solution was heated at 55-60° C. with stirring for 15 min and acidified with 35% HCl (1.5 ml) in hot. The suspension was stirred at 50-70° C. preferably at 60° C. for at least 30 min, cooled at room temperature, filtered and washed with water (10 ml) to furnish the hydrate. The obtained hydrate was dried at <50° C. for 3 hrs in vacuum at 50 mm of Hg to obtain constant weight. Yield 0.7 g (70%).

M.p.248-52° C., moisture content 0.9-1.04% (by Karl Fisher method), $[\alpha]_D^{26}$ −259.75° and HPLC 99.74%.

Figure 4:
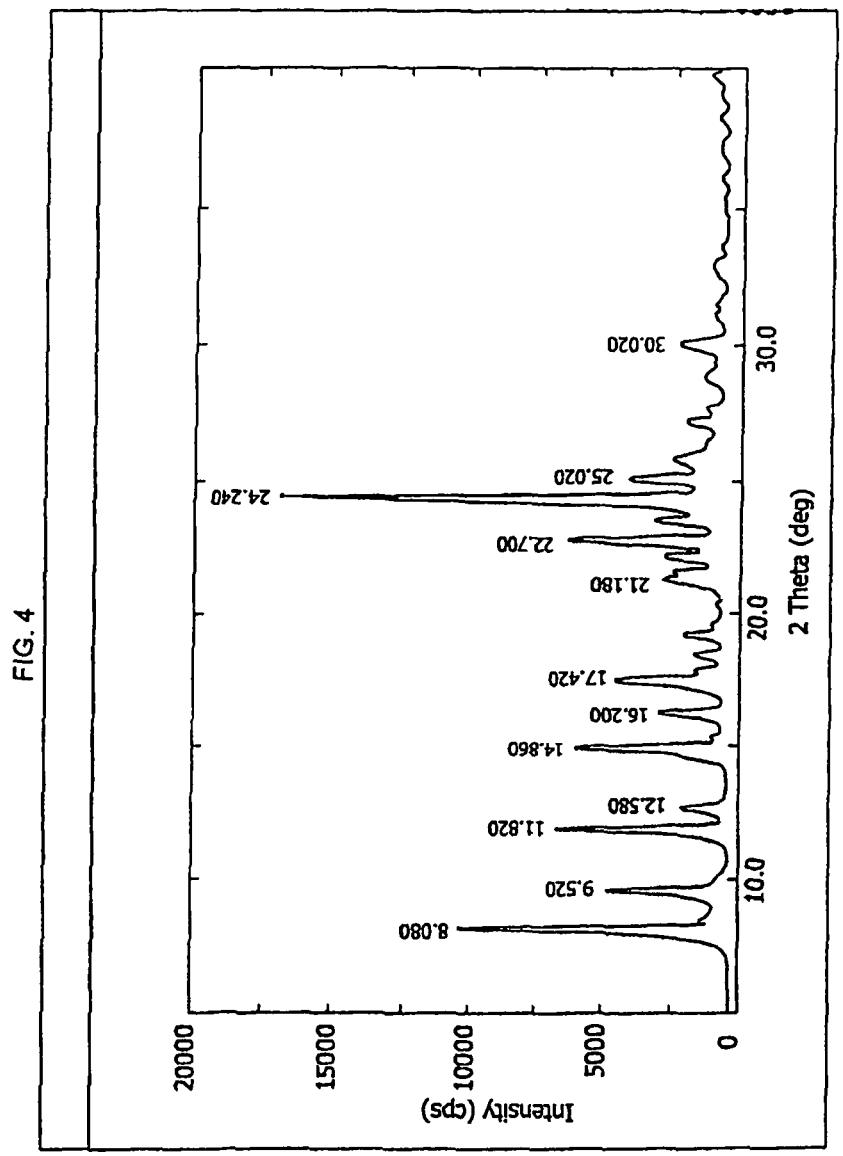
FIG. 4 represents the X-ray diffraction pattern of S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate.
5.
Figure 8:
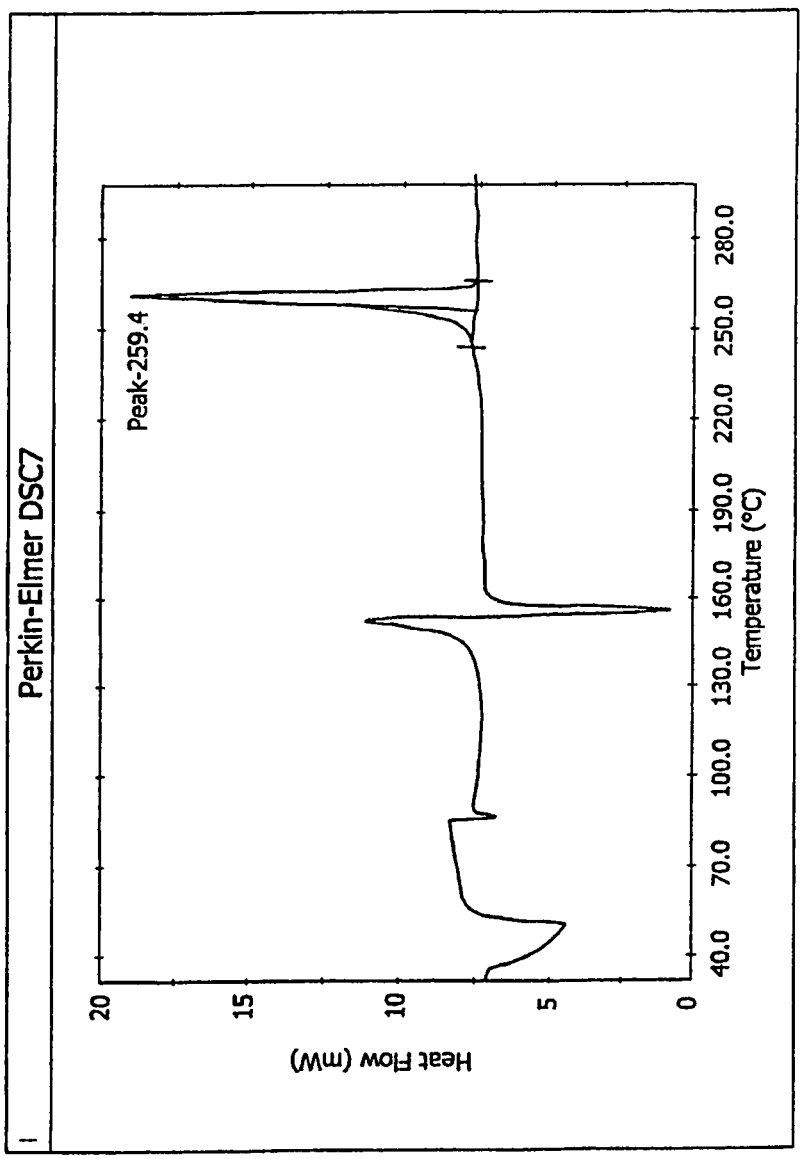
FIG. 8 represents the results of Differential Scanning Calorimetry on S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate.
9.

The X-ray diffraction pattern and the DSC analysis of the sample were identical to that of the 0.2 hydrate shown in FIG. 4 and FIG. 8 respectively.

Example 3

S-(−)-9-fluoro-6,7-dihydro-8-(4-hydroxypiperidin-1-yl)-5-methyl-1-oxo-1H,5H-benzo[i,j]quinolizine-2-carboxylic acid 0.5 hydrate(hemihydrate)

S-(−)-9-fluoro-6,7-dihydro-8-(4-hydroxypiperidin-1-yl)-5-methyl-1-oxo-1H,5H-benzo[i,j]quinolizine-2-carboxylic acid (8.0 g) was suspended in acetone (400 ml) and refluxed to obtain a clear solution. Heating was stopped and water (1500 ml) was added. The obtained mixture was kept over night at 5° C. The solid thus separated was filtered, washed with chilled acetone (5 ml) and dried at room temperature for 48 hr to obtain constant weight. Yield 6.2 g (77.5%).

M.p.256-58° C., moisture content 2.42% (by Karl Fisher method), HPLC purity 99.34% and $[\alpha]_D^{26}$ −260°.

Figure 5:
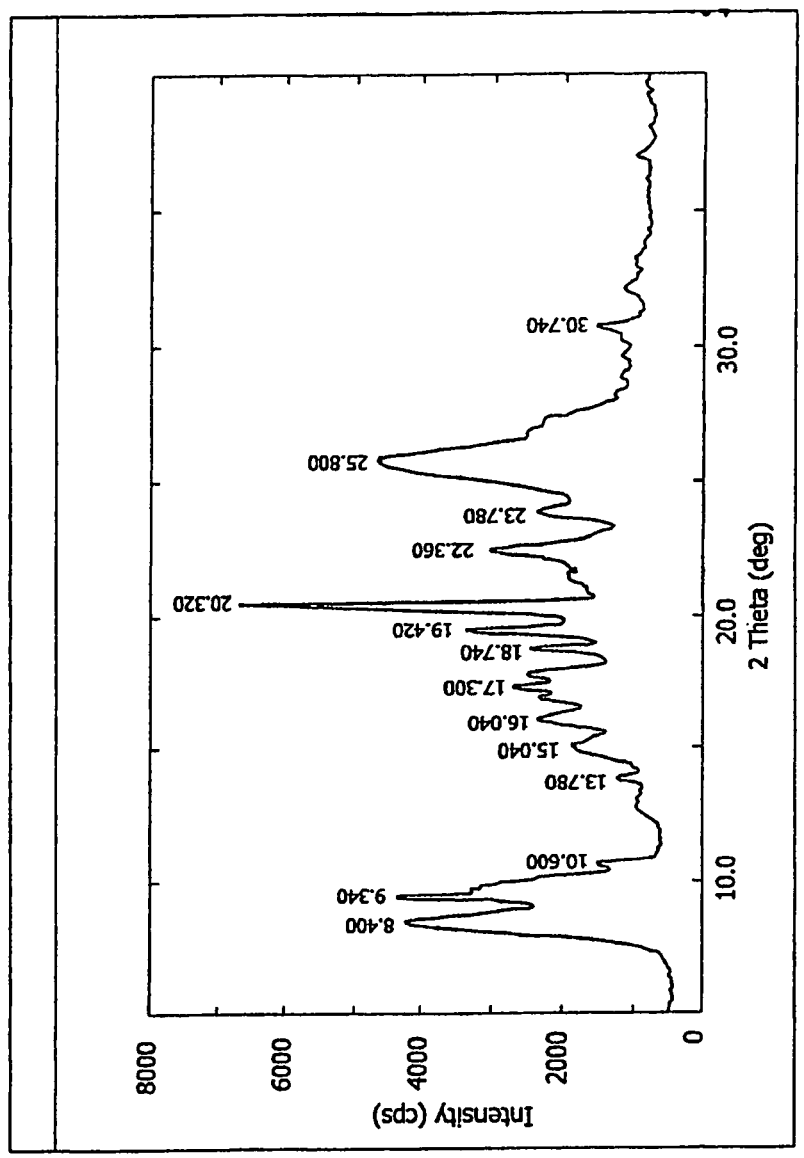
FIG. 5 represents the X-ray diffraction pattern of S-(−)-9-fluoro-6,7-dihydro-8-(4-hydroxypiperidin-1-yl)-5-methyl-1-oxo-1H,5H-benzo[i,j]quinolizine-2-carboxylic acid 0.5 hydrate.
6.
Figure 9:
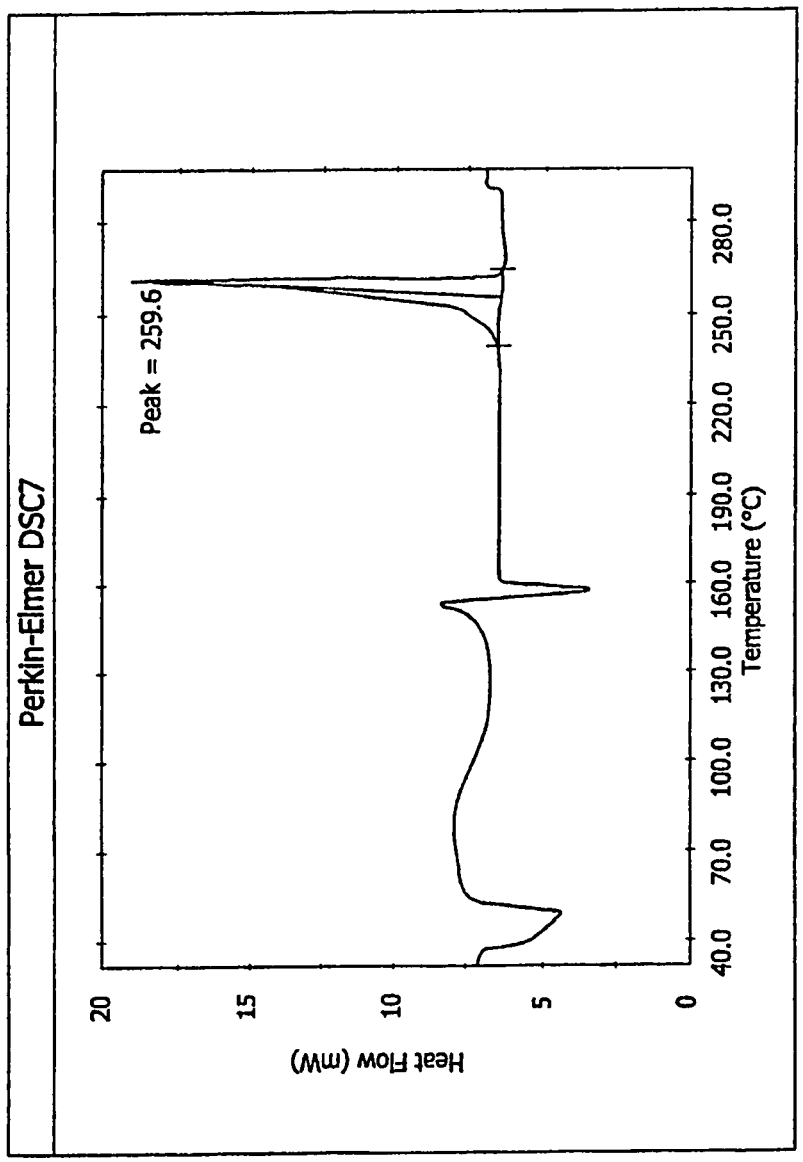
FIG. 9 represents the results of Differential Scanning Calorimetry on S-(−)-9-fluoro-6,7-dihydro-8-(4-hydroxypiperidin-1-yl)-5-methyl-1-oxo-1H,5H-benzo[i,j]quinolizine-2-carboxylic acid 0.5 hydrate.
10.

The X-ray diffraction pattern and the DSC analysis of the sample were identical to that of the hemihydrate shown in FIG. 5 and FIG. 9 respectively.

Example 4

S-(−)-9-fluoro-6,7-dihydro-8-(4-hydroxypiperidin-1-yl)-5-methyl-1-oxo-1H,5H-benzo[i,j]quinolizine-2-carboxylic acid 0.75 hydrate (hemisesquihydrate)

S-(−)-9-fluoro-6,7-dihydro-8-(4-hydroxypiperidin-1-yl)-5-methyl-1-oxo-1H,5H-benzo[i,j]quinolizine-2-carboxylic acid (10.0 g) was suspended in water (100 ml) and formulated into a slurry over a period of at least 1 hr with vigorous stirring. The obtained slurry was stirred at 5° C. for 1 hr, acetone (200 ml) was added and stirring continued at 5° C. for at least 4 hr. The solid thus separated was filtered, washed with chilled acetone (5 ml) and dried at room temperature for 24 hr to obtain constant weight. Yield 2.95 g (30%).

M.p.256-58° C., moisture content 3.294% (by Karl Fisher method) HPLC purity 99.44% and $[\alpha]_D^{26}$ −253°.

Figure 6:
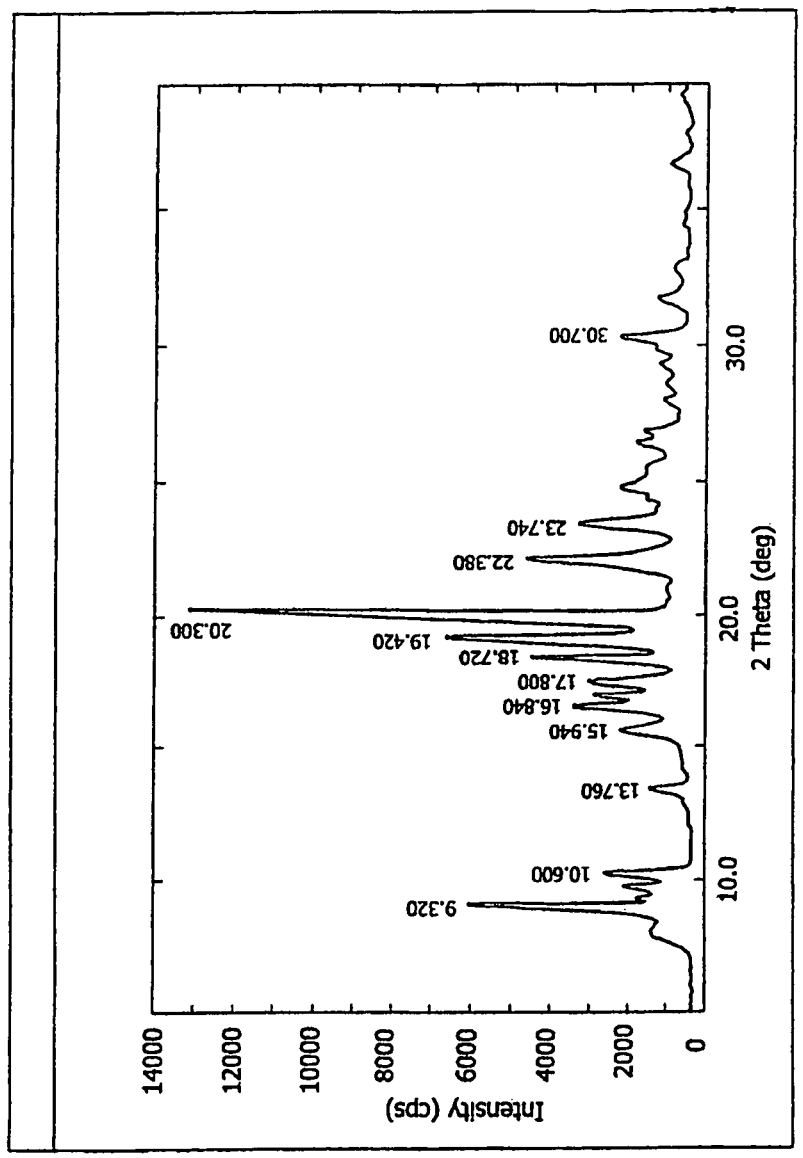
FIG. 6 represents the X-ray diffraction pattern of S-(−)-9-fluoro-6,7-dihydro-8-(4-hydroxypiperidin-1-yl)-5-methyl-1-oxo-1H,5H-benzo[i,j]quinolizine-2-carboxylic acid 0.75 hydrate.
7.
Figure 10:
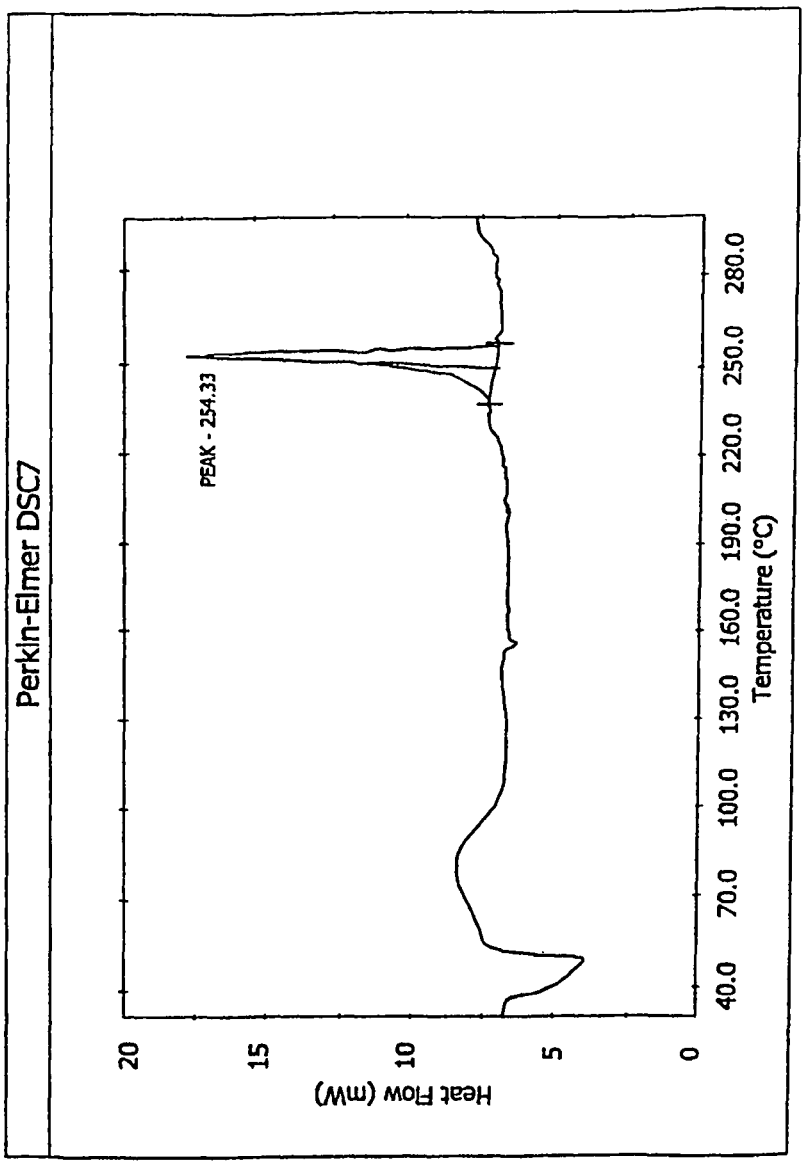
FIG. 10 represents the results of Differential Scanning Calorimetry on S-(−)-9-fluoro-6,7-dihydro-8-(4-hydroxypiperidin-1-yl)-5-methyl-1-oxo-1H,5H-benzo[i,j]quinolizine-2-carboxylic acid 0.75 hydrate.

The X-ray diffraction pattern and the DSC analysis of the sample were identical to that of the hemisesquihydrate shown in FIG. 6 and FIG. 10 respectively.

Example 5

S-(−)-9-fluoro-6,7-dihydro-8-(4-hydroxypiperidin-1-yl)-5-methyl-1-oxo-1H,5H-benzo[i,j]quinolizine-2-carboxylic acid, sodium salt monohydrate Method A:
S-(−)-9-fluoro-6,7-dihydro-8-(4-hydroxypiperidin-1-yl)-5-methyl-1-oxo-1H,5H-benzo[i,j]quinolizine-2-carboxylic acid (1.0-g, 2.777 mmole) was dissolved in acetonitrile (100 ml) at 90° C. to obtain clear solution, aqueous NaOH (2.67 ml, 1.04 mole) was added dropwise, the mixture was refluxed for 30 min and allowed to cool at room temperature for crystallization. The crystals thus separated were filtered and dried at 50° C. for 3 hr in vacuum at 50 mm of Hg to obtain constant weight. Yield 0.86 g (81%).

Method B:
The experiment was repeated using acetone in place of acetonitrile to give the same product Method C:
Aqueous sodium hydroxide solution (1N, 1.39 ml, 1.39 mmol) was added to the stirred powder of S-(−)-9-fluoro-6,7-dihydro-8-(4-hydroxypiperidin-1-yl)-5-methyl-1-oxo-1H,5H-benzo[i,j]quinolizine-2-carboxylic acid (0.5 g, 1.39 mmol) and diluted with water (10 ml). The resulting solution was stirred for 30 min., passed through micro filter and freeze dried to furnish S-(−)-9-fluoro-6,7-dihydro-8-(4-hydroxypiperidin-1-yl)-5-methyl-1-oxo-1H,5H-benzo[i,j]quinolizine-2-carboxylic acid sodium salt monohydrate. Yield 0.54 g (98%).

M.p.285° C. (dec), m/z 383 (M+H), $[\alpha]_D^{21}$-261° (1% water solution), solubility >1000 mg/ml in water, PMR ($D_2O$) δppm: 1.29 (3H, d, j=7.0 Hz, $CH_3$), 1.43-1.65 (2H, m, $H_6$), 1.65-2.1 (4H, m, $H_{3'}$ and $H_{5'}$), 2.6-3.2 (6H, m, $H_{2'}$, $H_{6'}$ and $H_7$), 3.71 (1H, m, $H_{4'}$), 4.47 (1H, m, $H_5$), 7.63 (1H, d, J=16.5 Hz, $H_{10}$) 8.32 (1H, S, $H_3$), moisture content 5.06% (by Karl Fisher method) and HPLC purity 98.7%.

Example 6

S-(−)-9-fluoro-6,7-dihydro-8-(4-hydroxypiperidin-1-yl)-5-methyl-1-oxo-1H,5H-benzo[i,j]quinolizine-2-carboxylic acid potassium salt monohydrate Aqueous potassium hydroxide solution (0.5%, 15.6 ml, 1.39 mmol) was added to the stirred powder of S-(−)-9-fluoro-6,7-dihydro-8-(4-hydroxypiperidin-1-yl)-5-methyl-1-oxo-1H,5H-benzo[i,j]quinolizine-2-carboxylic acid (0.5 g, 1.39 mmol). The resulting solution was stirred for 30 min., passed through micro filter and freeze dried to provide S-(−)-9-fluoro-6,7-dihydro-8-(4-hydroxypiperidin-1-yl)-5-methyl-1-oxo-1H,5H-benzo[i,j]quinolizine-2-carboxylic acid potassium salt Yield 0.568 g (99%), m.p. >300° C., m/z 399 (M+H), $[\alpha]_D^{25}$ −255° (1% water solution), solubility >1000 mg/ml in water, PMR (DMSO-$d_6$) δppm: 1.3 (3H, d, j=6.8 Hz, $CH_3$), 1.4-1.7 (2H, m, $H_6$), 1.7-1.95 (2H, m, $H_{3'}$ and $H_{5'}$), 1.95-2.2 (2H, m, $H_{3'}$ and $H_{5'}$), 2.75-2.98 (2H, m, $H_{2'}$ and $H_7$), 2.98-3.3 (4H, m, $H_{2'}$, $H_{6'}$ and $H_7$), 4.1 (1H, m, $H_{4'}$), 4.5 (1H, m, $H_5$), 7.84 (1H, d, J=12.6 Hz, $H_{10}$), 8.3 (1H, S, $H_3$).

Example 7

S-(−)-9-fluoro-6,7-dihydro-8-(4-hydroxypiperidin-1-yl)-5-methyl-1-oxo-1H,5H-benzo[i,j]quinolizine-2-carboxylic acid, L-arginine salt 0.25 hydrate Aqueous L-arginine solution (1%, 24.2 ml, 1.39 mmol) was added to the stirred solution of S-(−)-9-fluoro-6,7-dihydro-8-(4-hydroxypiperidin-1-yl)-5-methyl-1-oxo-1H,5H-benzo[i,j]quinolizine-2-carboxylic acid (0.5 g, 1.39 mmol) in methanol (20 ml). The resulting solution was stirred for 30 min., passed through a micro filter and concentrated to dryness to furnish S-(−)-9-fluoro-6,7-dihydro-8-(4-hydroxypiperidin-1-yl)-5-methyl-1-oxo-1H,5H-benzo[i,j]quinolizine-2-carboxylic acid, L-arginine salt. Yield 0.7 g (93.4%), m.p. 255-60° C., m/z 535 (M+H), $[\alpha]_D^{25}$-193.3° (1% methanol solution) solubility >75 mg/ml in water, PMR ($D_2O$) δppm: 1.32 (3H, d, j=6.8 Hz, $CH_3$), 1.5-1.7 (2H, m, $H_6$), 1.7-2.2 (8H, m, H$_3$, H$_5$, and 2XCH$_2$), 2.7-3.3 (8H, m, H$_2$, H$_6$, H$_7$ and NCH$_2$), 3.5 (1H, m, CH), 3.75 (1H, m, H$_4$), 4.5 (1H, m, H$_5$), 7.85 (1H, d, J=12.6 Hz, H$_{10}$), 8.5 (1H, S, H$_3$).

Example 8

S-(−)-9-fluoro-6,7-dihydro-8-(4-hydroxypiperidin-1-yl)-5-methyl-1-oxo-1H,5H-benzo[i,j]quinolizine-2-carboxylic acid, L-arginine salt 0.75 hydrate L-(+)-Arginine (0.958 g., 5.5 mmoles) was added in portions to a suspension solution of S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate (2.0 g., 5.5 mmole) in methanol (400 ml). The obtained solution was concentrated in vacuum to give the desired product as a yellow solid, which was dried at 50° C. at 50 mm/Hg for 5 hours. Yield 3.0 g. (100%), m.p. 220-223° C. (dec), m/z 535 (M+H), moisture content 2.3% (by Karl Fisher, required 2.46%), $[\alpha]_D^{25}$ −144° (1% methanol c=1), solubility 93 mg/ml.

Examples 9 & 10

Similarly prepared were S-(−)-9-fluoro-6,7-dihydro-8-(4-hydroxypiperidin-1-yl)-5-methyl-1-oxo-1H,5H-benzo[i,j]quinolizine-2-carboxylic acid L-lysine salt monohydrate, and S-(−)-9-fluoro-6,7-dihydro-8-(4-hydroxypiperidin-1-yl)-5-methyl-1-oxo-1H,5H-benzo[i,j]quinolizine-2-carboxylic acid L-histidine salt 0.2 hydrate.

S-(−)-9-fluoro-6,7-dihydro-8-(4-hydroxypiperidin-1-yl)-5-methyl-1-oxo-1H,5H-benzo[i,j]quinolizine-2-carboxylic acid L-lysine salt monohydrate Yield 0.7 g (99%), m.p. 235-40° C., m/z 506 (M+H), $[\alpha]_D^{25}$ −177° (1% methanol solution) solubility 75 mg/ml in water. PMR (DMSO-d$_6$) δppm: 1.38 (3H, d, j=6.8 Hz, CH$_3$), 1.48-2.25 (10H, m, H$_3$, H$_5$, H$_6$ and 2XCH$_2$), 2.5-2.83 (4H, m, 2X CH$_2$), 2.85-3.4 (6H, m, H$_2$, H$_6$, and H$_7$), 3.72-3.88 (2H, m, H$_4$, and CH), 4.75 (1H, m, H$_5$), 7.78 (1H, d, J=12.6 Hz, H$_{10}$), 8.8 (1H, S, H$_3$).

S-(−)-9-fluoro-6,7-dihydro-8-(4-hydroxypiperidin-1-yl)-5-methyl-1-oxo-1H,5H-benzo[i,j]quinolizine-2-carboxylic acid L-histidine salt 0.2 hydrate Yield 0.67 g (94%), m.p. 270-80° C., m/z 515 (M+H), $[\alpha]_D^{25}$ −216° (1% methanol solution) solubility 75 mg/ml in water, PMR (DMSO-d$_6$) δppm: 1.42 (3H, d, j=6.8 Hz, CH$_3$), 1.48-1.70 (2H, m, H$_6$), 1.75-2.23 (4H, m, H$_3$, and H$_5$), 2.78-3.31 (6H, m, H$_2$, H$_6$, and H$_7$), 3.5 (1H, m, CH), 3.71 (2H, m, CH$_2$), 4.15 (1H, m, H$_4$), 4.78 (1H, m, H$_5$), 6.9 (1H, s, imidazole H), 7.62 (1H, s, imidazole H), 7.83 (1H, d, J=12.5 Hz, H$_{10}$) 8.86 (1H, S, H$_3$).

Example 11

Pivaloyloxymethyl S-(−)-9-fluoro-6,7-dihydro-8-(4-hydroxypiperidin-1-yl)-5-methyl-1-oxo-1H,5H-benzo[i,j]quinolizine-2-carboxylate S-(−)-9-fluoro-6,7-dihydro-8-(4-hydroxypiperidin-1-yl)-5-methyl-1-oxo-1H,5H-benzo[i,j]quinolizine-2-carboxylic acid (1.0 g, 2.77 mmol) was dissolved in N,N-dimethyl formamide (25 ml) and solution was stirred at 50° C. Powdered anhydrous potassium carbonate (0.385 g, 2.77 mmol) was added to stirred solution and stirring was continued for 6 hr at 50° C. Chloro methyl pivalate (2.0 g, 13.88 mmol) was added to the resulting mixture and stirred for 40 h at 50° C. The reaction mixture was concentrated, triturated with water, extracted with chloroform to give crude product, which was purified by chromatography. Yield 0.9 g (71%), m.p 198-200° C., m/z 475(M+H).

Example 12

Similarly prepared to the product of Example 11 were Acetoxymethyl S-(−)-9-fluoro-6,7-dihydro-8-(4-hydroxypiperidin-1-yl)-5-methyl-1-oxo-1H,5H-benzo[i,j]quinolizine-2-carboxylate. Chloromethyl acetate was used in place of chloromethyl pivalate. Yield 0.35 g (56%), m.p. 180° C., m/z 433(M+1), $[\alpha]_D^{22.5}$ −251° (1% CHCl$_3$ solution).

Example 13

Similarly prepared to the product of Example 11 was Pivaloyloxyethyl S-(−)-9-fluoro-6,7-dihydro-8-(4-hydroxypiperidin-1-yl)-5-methyl-1-oxo-1H,5H-benzo[i,j]quinolizine-2-carboxylate. Chloroethyl pivalate was used in place of chloromethyl pivalate. Yield 0.08 g (59%), m.p. 92-95° C., m/z 489(M+1), $[\alpha]_D^{22.5}$ −174.50° (0.4% methanol solution).

Example 14

Similarly prepared to the product of Example 11 was Propionoxymethyl S-(−)-9-fluoro-6,7-dihydro-8-(4-hydroxypiperidin-1-yl)-5-methyl-1-oxo-1H,5H-benzo[i,j]quinolizine-2-carboxylate. Bromoethyl acetate was used in place of chloromethyl pivalate. Yield 0.4 g (67%), m.p. 185-187° C., m/z 447 (M+1), $[\alpha]_D^{22.5}$ −186° (1% chloroform solution).

Example 15

Carboxymethyl S-(−)-9-fluoro-6,7-dihydro-8-(4-hydroxypiperidin-1-yl)-5-methyl-1-oxo-1H,5H-benzo[i,j]quinolizine-2-carboxylate (sodium salt)

S-(−)-9-fluoro-6,7-dihydro-8-(4-hydroxypiperidin-1-yl)-5-methyl-1-oxo-1H,5H-benzo[i,j]quinolizine-2-carboxylic acid (0.72 g, 2 mmol) was dissolved in N,N-dimethyl formamide (25 ml) and solution was stirred at 50° C. Powdered anhydrous potassium carbonate (0.385 g, 2.77 mmol) was added to stirred solution and stirring was continued for 6 hr at 50° C. Bromo acetic acid t-Butyl ester (1.9 g, 10 mmol) was added to the resulting mixture and stirred for 40 h at 50° C. The reaction mixture was concentrated, triturated with water, extracted with chloroform to give crude product, which was purified by chromatography. Yield 0.76 g (80%).

The t-Butyl group was removed by treatment with trifluoroacetic acid to get the desired product.

Example 16

S-(−)-9-fluoro-6,7-dihydro-8-(4-methoxypiperidin-1-yl)-5-methyl-1-oxo-1H,5H-benzo[i,j]quinolizine-2-carboxylic acid A mixture of S-(−)-diacetoxy-(8,9-difluoro-6,7-dihydro-1-oxo-1H,5H-benzo[i,j]quinolizine-2-carboxyl)borane (0.2 g, 0.49 mmol) and 4-methoxypiperidine (0.226 g, 1.9 mmol) in acetonitrile (8 ml) was stirred at 100° C. for 24 h. The reaction mixture was concentrated, triturated with water and filtered. The obtained solid was dissolved in acetonitrile (8 ml), treated with 1N aqueous NaOH solution (10 ml) and stirred to obtain a clear solution. The resulting solution was acidified with conc. HCl, the separated precipitate was filtered, washed with water and dried. The obtained crude product was purified by chromatography. Yield 0.07 g (38%), m.p 194° C., m/z 375(M+H), $[\alpha]_D^{26}$ −209.75° (0.5% methanol solution), PMR (CDCl$_3$) δppm: 1.55 (3H, d, j=6.8 Hz, CH$_3$), 1.8-1.9 (2H, m, H$_6$), 1.9-2.3 (4H, m, H$_3$, and H$_5$), 2.8-3.2 (6H, m, $H_{2'}$, $H_{6'}$ and $H_7$), 3.25 (1H, m, $H_{4'}$), 3.45 (3H, s, $CH_3$), 4.55 (1H, m, H), 8.2 (1H, d, J=16.5 Hz, $H_{10}$), 8.7 (1H, S, $H_3$), 15.1 (1H, bs, COOH $D_2O$ exchangeable).

Example 17

S-(−)-9-fluoro-6,7-dihydro-8-(4-acetoxypiperidin-1-yl)-5-methyl-1-oxo-1H,5H-benzo[i,j]quinolizine-2-carboxylic acid Acetic anhydride (0.312 g, 3.6 mmol) was added to a stirred mixture of S-(−)-9-fluoro-6,7-dihydro-8-(4-hydroxypiperidin-1-yl)-5-methyl-1-oxo-1H,5H-benzo[i,j]quinolizine-2-carboxylic acid (0.65 g, 1.8 mmol) and N,N-4-dimethylaminopyridine (0.01 g) in pyridine (10 ml), stirring was continued for 3 h at ambient temperature. The reaction mixture was concentrated, triturated with water, filtered, washed with water and dried. The obtained crude product was purified by chromatography. Yield 0.69 g (95%), m.p 230-35° C., m/z 403(M+H), $[\alpha]D_{25}$ −239° (1% methanol solution), PMR ($CDCl_3$) δppm: 1.51 (3H, d, j=6.8 Hz, $CH_3$), 1.85-1.9 (2H, m, $H_6$), 2.1 (3H, s, $COCH_3$), 1.9-2.3 (4H, m, $H_3$, and $H_{5'}$), 2.9-3.4 (6H, m, $H_{2'}$, $H_{6'}$ and $H_7$), 4.5 (1H, m, $H_5$), 5.0 (1H, m, $H_{4'}$), 8.2 (1H, d, J=16.5 Hz, $H_{10}$), 8.7 (1H, S, $H_3$) 15.1 (1H, bs, COOH, $D_2O$ exchangeable).

Example 18

S-(−)-9-fluoro-6,7-dihydro-8-(4-pivaloyloxypiperidin-1-yl)-5-methyl-1-oxo-1H,5H-benzo[i,j]quinolizine-2-carboxylic acid Pivaloyl chloride (0.08 g, 0.66 mmol) was added to a stirred mixture of S-(−)-9-fluoro-6,7-dihydro-8-(4-hydroxypiperidin-1-yl)-5-methyl-1-oxo-1H,5H-benzo[i,j]quinolizine-2-carboxylic acid (0.08 g, 0.22 mmol) and N,N4-dimethylaminopyridine (0.005 g) in pyridine (5 ml), stirring was continued for 3 h at ambient temperature. The reaction mixture was concentrated, triturated with water, filtered, washed with water and dried. The obtained crude product was purified by chromatography. Yield 0.05 g (50%), m.p 200-05° C., m/z 445(M+H), $[\alpha]_D^{26}$ −199.5°(0.5% methanol solution), PMR ($CDCl_3$) δppm: 1.26 (9H, S, 3 X $CH_3$), 1.57 (3H, d, j=6.8 Hz, $CH_3$), 1.8-1.95 (2H, m, $H_6$), 1.95-2.36 (4H, m, $H_3$, and $H_{5'}$), 2.9-3.5 (6H, m, $H_{2'}$, $H_{6'}$ and $H_7$), 4.58 (1H, m, $H_5$), 5.05 (1H, m, $H_{4'}$), 8.22 (1H, d, J=16.5 Hz, $H_{10}$), 8.74 (1H, S, $H_3$).

Example 19

S-(−)-9-fluoro-6,7-dihydro-8-(4-[(β-D-tetraacetyl-glucopyranosyl)oxy]-piperidin-1-yl)-5-methyl-1-oxo-1H,5H-benzo[i,j]quinolizine-2-carboxylic acid A solution of acetobromoglucose (1.71 g., 4.16 mmol) in dichloroethane (20 ml.) was added to S-(−)-9-fluoro-6,7-dihydro-8-(4-hydroxypiperidin-1-yl)-5-methyl-1-oxo-1H,5H-benzo[i,j]quinolizine-2-carboxylic acid (1.0 g, 2.77 mmol), 4° A molecular sieves (~100 g) and silver carbonate (3.066 g., 11.11 mmol). The reaction mixture was heated at 60-70° C. under argon atmosphere for 20 hrs. in the dark. The solids were filtered off and the filtrate was concentrated in vacuum to give the product. Column chromatography of the crude product gave the tetraacetate. Yield 1.75 g. m.p 157-158° C., m/z 691(M+H), $[\alpha]D_{26}$ −199.5° (0.5% methanol solution), PMR ($CDCl_3$) δppm: 1.42 (3H, d, j=6.8 Hz, $CH_3$), 1.73-1.98 (2H, m, $H_6$), 2.01 (3H, s, COCH3) 2.20 (9H, s, 3xCOCH3), 2.60-3.40 (8H, m), 3.80-4.52 (7H, m), 5.46-5.42 (4H, m) 5.98 (1H, d, J=10.1 Hz), 7.91 (1H, d, J=12.5 Hz), 8.77 (1H, s).

Example 20

S-(−)-9-fluoro-6,7-dihydro-8-(4-[(β-D-glucopyranosyl)oxy]-piperidin-1-yl)-5-methyl-1-oxo-1H,5H-benzo[i,j]quinolizine-2-carboxylic acid S-(−)-9-fluoro-6,7-dihydro-8-(4-[(β-D-tetraacetylglucopyranosyl)oxy]-piperidin-1-yl)-5-methyl-1-oxo-1H,5H-benzo[i,j]quinolizine-2-carboxylic acid (0.144 g., 0.20 mmol) was dissolved in a 3:1 mixture of methanol and water. Lithium hydroxide (87 mg., 2.00 mmol) was added to the solution and the mixture was stirred at room temperature for 0.5 hr. The mixture was evaporated to dryness and the residue was dissolved in small amount of methanol, filtered and the filtrate was evaporated to give the product.

Examples 21 to 23

General method for making amides of S-(−)-9-fluoro-8(4-hydroxypiperidin-1-yl)-5-methyl-6,7-dihydro-1-oxo-1H, 5H-benzo[i,j]quinolizine-2-carboxylic acid with an amino acid e.g. glutamic acid.

9-fluoro-8(4-hydroxypiperidin-1-yl)-5(S)-methyl-6,7-dihydro-1-oxo-1H,5H-benzo[i,j]quinolizine-2-[2(S)-amino-1, 5-pentanedioic acid]carboxamide, disodium salt:

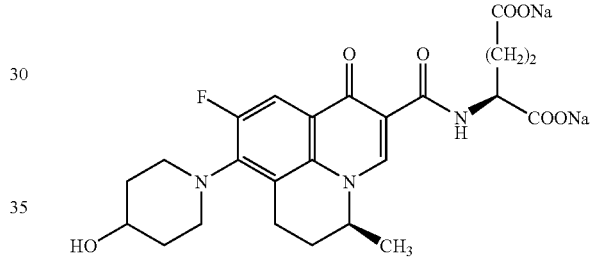

S-(−)-9-Fluoro-8(4-hydroxypiperidin-1-yl)-5-methyl-6,7-dihydro-1-oxo-1H,5H-benzo[i,j]quinolizine-2-carboxylic acid (360 mg, 1.0 mmol) and triethylamine (0.145 ml, 1.0 mmol) were dissolved in dimethylacetamide (15 ml). Isobutylchloroformate (0.13 ml, 1.0 mmol) was added under ice cooling and stirred for 5 min. A solution of S-glutamic acid dimethyl ester hydrochloride (422 mg, 2.0 mmol) and triethylamine (2 mmol, 0.28 ml) in dimethylacetamide (10 ml) was added, followed by addition of 4-(dimethylamino) pyridine (125 mg, 1.0 mmol) and the mixture was stirred at RT overnight. The reaction mixture was diluted with ethyl acetate (50 ml), washed with 0.5 N HCl, saturated $NaHCO_3$ solution, brine, dried ($Na_2SO_4$) and evaporated under vacuum. The residue was dissolved in methanol (10 ml), added 1N NaOH (1.1 ml) and stirred for 2-3 h at RT. The reaction mixture was concentrated, acidified with 1N HCl and dissolved in ethyl acetate (50 ml). The organic layer was washed with brine, dried ($Na_2SO_4$), solvent was evaporated, residue purified by column chromatography and freeze dried to give the free acid. Yield (150 mg, 30%). Dissolved the free acid (150 mg, 0.3 mmol) and $NaHCO_3$ (50 mg, 0.6 mmol) in water and freeze dried to give the product.

Similarly made were amides using the amino acids such as alanine and histidine.

Examples 24-37

General method for making the amino acid esters of the 4' hydroxy of piperidinyl moiety of S-(−)-9-Fluoro-8(4-hydroxypiperidin-1-yl)-(5S)-methyl-6,7-dihydro-1-oxo-1H,5H-benzo[i,j]quinolizine-2-carboxylic acid, e.g. the lysine ester.

8-{4-2(S),6-Diaminohexanoyloxy]piperidin-1-yl}-9-fluoro-5(S)-methyl-6,7-dihydro-1-oxo-1H,5H-benzo[i,j]quinolizine-2-carboxylic acid, dihydrochloride:

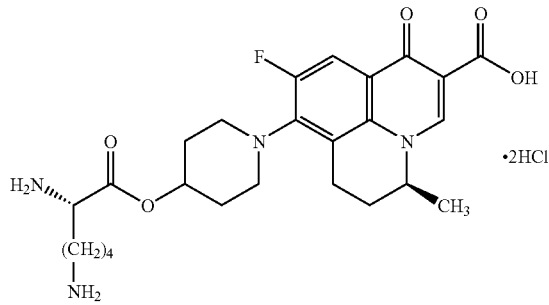

S(−)-9-Fluoro-8(4-hydroxypiperidin-1-yl)-5-methyl-6,7-dihydro-1-oxo-1H,5H-benzo[i,j]quinolizine-2-carboxylic acid (360 mg, 1.0 mmol) and triethylamine (0.14 ml, 1.0 mmol) were dissolved in dimethylacetamide (15 ml). Bis-t-butyloxycarbonyl-S-lysine (415 mg, 1.2 mmol) and 4-(dimethylamino)pyridine (150 mg, 1.2 mmol) were added, followed by the addition 1,3-dicyclohexylcarbodiimide (206 mg, 1.0 mmol) under ice cooling. The reaction mixture was stirred for 30 minutes at 0° C. followed by overnight stirring at RT. The reaction mixture was filtered, diluted with ethyl acetate, washed with 0.5 N HCl, saturated NaHCO$_3$ solution, brine, dried (Na$_2$SO$_4$) and evaporated to give residue. The residue was treated with trifluoroacetic acid (10 ml), stirred the mixture at RT for 30 min. and evaporated under reduced pressure. The residue was triturated with ether to give the precipitated. The precipitates were further purified by column chromatography, dissolved in 0.1 N HCl and freeze dried to give the product. Yield (374 mg, 69%)

Similarly esters were made with the following amino acids: S-Ala, S-Ala-S-Ala, R-Ala, R-Ala-R-Ala, N-Methyl S-Ala, S-Leu, R-Leu, S-Phe, S-Pro, S-Asp, Nitro-S-Arg, S-Arg, Nitro-S-Arg-Nitro-S-Arg, S-Arg-S-Arg, The data corresponding to the respective compounds made are provided in the following table:

| Amino acid linked at 4-OH group of Example 1 compound | Salt | Yield % | Melting Point ° C. | MASS (M + H) | HPLC Purity (%) | Moisture Content |
|---|---|---|---|---|---|---|
| 25. S-Ala | HCl, H$_2$O | 95 | 160-5(d) | 432 | 99.0 | 3.4 |
| 26. R-Ala | HCl, H$_2$O | 92 | 225 | 432 | 99.0 | 4.7 |
| 27. R-Ala-S-Ala | HCl, 0.5H$_2$O | 90 | 190-93 | 503 | 97.0 | 1.1 |
| 28. R-Leu | HCl, H$_2$O | 94 | 220-33 | 474 | 99.0 | 3.4 |
| 29. N-Me-S-Ala | HCl, 0.5H$_2$O | 91 | 140-50 | 446 | 97.5 | 1.9 |
| 30. R-Ala | AcOH | 98 | 125-27 | 432 | 99.7 | — |
| 31. S-Val | HCl, 0.75H$_2$O | 93 | 160-61 | 460 | 96.2 | 2.7 |
| 32. S-Ala-S-Ala | HCl | 60 | 175-80 | 503 | 97.8 | — |
| 33. R-Ala-R-Ala | HCl | 75 | 95-100 | 503 | 98.0 | — |
| 34. S-Arg (Nitro) | HCl | 70 | 113-16 | 588 | 93.0 | — |
| 35. S-Arg | HCl | 70 | 178-82 | 603 | 94.0 | — |
| 36. [S-Arg(Nitro)]$_2$ | HCl | | | | | |
| 37. S-Arg-S-Arg | 3HCl | | | | | |

BIOLOGICAL EXAMPLES

Microbiological and pharmacological studies can be used to determine the relative potency, and the profile of specificity of the optically pure enantiomers, and the racemic mixture of Nadifloxacin as antibacterial agent with a spectrum of activity as described in the specification above.

Biological Example 1

In-Vitro Antimicrobial Activity Test

The activity of the compounds of the invention in vitro can be illustrated as follows:

The comparative antimicrobial activity of S-(−)-Nadifloxacin, RS-(±)-Nadifloxacin, Mupirocin and Levofloxacin against various microorganisms is given in Table 1. The test method was in accordance with the standard NCCLS protocol.

TABLE 1

Comparative MICs (μg/ml) of S-(−)-Nadifloxacin, RS-(±)-Nadifloxacin, Mupirocin and Levofloxacin

| ORGANISMS | S-(−)-NADIFLOXACIN | RS-(±)-NADIFLOXACIN | MUPIROCIN | LEVOFLOXACIN |
|---|---|---|---|---|
| *Staphylococcus aureus* ATCC 25923 | 0.025 | 0.05 | 0.4 | 0.2 |
| MRSA STA-4 | 0.4 | 0.8 | 0.4 | >12.5 |
| MRSE STE-22 | 0.4 | 1.56 | 0.2 | >12.5 |

TABLE 1-continued

Comparative MICs (µg/ml) of S-(−)-Nadifloxacin, RS-(±)-Nadifloxacin, Mupirocin and Levofloxacin

| ORGANISMS | S-(−)-NADIFLOXACIN | RS-(±)-NADIFLOXACIN | MUPIROCIN | LEVOFLOXACIN |
|---|---|---|---|---|
| Mupirocin-resistant Staph STA-34 | 0.4 | 1.56 | >400 | 12.5 |
| Propioni bacterium acnes | 0.1 | 0.2 | >1000 | 1.0 |
| Streptococcus pneumoniae ATCC 6303 | 0.2 | 0.4 | 0.2 | 0.8 |
| Streptococcus pyogenes | 0.2 | 0.4 | 0.025 | 0.4 |
| Viridans group Streptococci | 0.2 | 0.4 | 0.2 | 1.56 |
| Enterococcus faecalis ATCC 29212 | 0.2 | 0.4 | >12.5 | 0.8 |
| Enterococcus faecium | 0.4 | 0.8 | >0.8 | 1.56 |
| Corynebacterium jeikeium | 0.05 | 0.2 | >12.5 | 0.4 |
| Haemophilus influenzae | 0.025 | 0.05 | N.A. | 0.03 |
| Escherichia coli ATCC 25922 | 0.2 | 0.8 | N.A. | 0.05 |
| Serratia marcescens | 0.4 | 1.56 | N.A. | 0.1 |
| Pseudomonas aeruginosa | 1.56 | 3.12 | N.A. | 3.12 |
| Bacteroides fragilis | 0.8 | 3.12 | N.A. | 6.25 |
| Mycobacterium tuberculosis ATCC 27294 | 0.8 | 1.56 | — | 0.4 |
| Mycobacterium intracellulare | 1.56 | 3.12 | — | 0.8 |
| Mycobacterium avium | 3.12 | 6.25 | — | 12.5 |
| Chryseobacterium meningosepticum | 0.8 | 1.56 | — | 6.25 |

1. Mupirocin resistant MRSA strains with very high MICs of >400 µg/ml can effectively be inhibited by S-(−)-Nadifloxacin or racemic Nadifloxacin at much lower MICs of 0.4-1.56 µg/ml. For such strains, levofloxacin is 30 times less active than S-(−)-Nadifloxacin and 8 times less active than RS(±)Nadifloxacin.
2. S-(−)-Nadifloxacin has 2-4 times higher activity than racemic-Nadifloxacin.
3. S-(−)-Nadifloxacin has 48 times higher activity than levofloxacin against nosocomial pathogens like enterococci and chryseobacterium meningosepticum.

Biological Example 2

Effect of pH on Potency of Fluoroquinolones

The test method was in accordance with the standard NCCLS protocol employing test media adjusted at pH 5.5 and 7.0.

TABLE 2

Effect of pH at 5.5 on % loss (−)/gain (+) in potency of Fluoroquinolones against Urinary Tract Pathogens

| ORGANISM | % CHANGE IN POTENCY AT pH 5.5* | | |
|---|---|---|---|
| | S-(−)-Nadi | Cipro | Levo |
| S. aureus 25923 | +100 | −75 | −75 |
| S. aureus 1199-B | +100 | −75 | −75 |
| E. faecalis | +100 | −87.5 | −75 |
| E. coli 2015 | +100 | −94 | −87.5 |
| E. coli 25922 | +100 | −97.5 | −96 |
| P. mirabilis 37 | +100 | −96 | −94 |
| P. rettgeri N 1764 | 0.00 | −94 | −94 |
| P. vulgaris 66 | +100 | −96 | −94 |
| Klebsiella 24037 | +100 | −97 | −94 |
| Serratia marcescens 2702 | 0.00 | −99 | −98 |
| Acinetobacter 3109 | +100 | −97 | −94 |
| Ps. Aeruginosa | +100 | −87 | −50 |

*% Change in Potency at pH 5.5 = 100 (−MIC pH 7/MIC pH 5.5 × 100)

Biological Example 3

Acute Toxicity

The acute intravenous toxicity of RS-(±)- and S-(−)-forms of Nadifloxacin in mice is shown in Table 3 below:

TABLE 3

| COMPOUND | $LD_{50}$ (mg/kg) |
|---|---|
| RS-(±)-Nadifloxacin | 311 |
| S-(−)-Nadifloxacin | >400* |

*$LD_{50}$ 400 mg/kg i.e. no mortality observed at a dose of 400 mg/kg.

Biological Example 4

Hepatotoxicity Differential Between S-(−)-Nadifloxacin and Trovafloxacin

Human Liver Cell Line Cytotoxicity Assay

The procedure involved cultivation of cells of human liver cell-line Hep-G2 in DMEM medium containing 5% foetal bovine and exposure to various concentrations of trovafloxacin and S-(−)-Nadifloxacin for 3 hours. The drug containing medium was then replaced with a fresh medium and cells were incubated in 5% CO2 atmosphere at 37° C. for 4 days. Almar blue dye which is an indicative of active respiration was then added to individual sample to access the toxicity of the drugs. The hepatotoxic potential of a drug is expressed in terms of Minimum Toxic Dose (MTD) which is defined as minimum concentration of a drug which brings about inhibition of color change from blue to pink.

Using above test method, S-(−)-Nadifloxacin was found to be tolerated well by Hep-G-2 Cells at dosages 4 times higher than trovafloxacin.

Biological Example 5

Bioavailability

The blood levels of RS-(±)-Nadifloxacin and S-(−)-Nadifloxacin administered orally to Swiss mice at a dose of 30 mg/kg are shown in Table 3 with respect to the AUC (μg/ml·hr), monitored from 15 minutes to 4 hours.

TABLE 4

| COMPOUNDS | AUC ((μg/ml.hr) |
|---|---|
| RS-(±)-Nadifloxacin | 16.9 |
| S-(−)-Nadifloxacin | 33.58 |

S-(−)-Nadifloxacin has increased oral bioavailability compared to racemic Nadifloxacin.

Biological Example 6

Effect of NorA Efflux Pump on Fluoroquinolone Potency

According to NCCLS protocols, comparative MICs were determined for S. aureus strain bearing Nor A efflux pump and a corresponding patent strain devoid of efflux pump. Using this set of MIC values, % loss in potency due to efflux was calculated for each of the fluoroquinolone in Table 5

TABLE 5

| Fluoroquinolone | % loss in potency for S. aureus bearing Efflux pump |
|---|---|
| S-(−)-Nadifloxacin | 0 |
| Norfloxacin | 97 |
| Ciprofloxacin | 94 |
| Levofloxacin | 75 |
| Gemifloxacin | 75 |
| Clinafloxacin | 87.5 |
| Gatifloxacin | 75 |

Biological Example 7

Fold Elevation in $ED_{50}$ Dose of Fluoroquinolones

For S. aureus with Nor A Efflux Pump

In mouse model of infection caused by S. aureus with and without efflux pump, 50% protective dosages were determined for Ciprofloxacin, Ofloxacin, Levofloxacin and S-(−)-Nadifloxacin. From these experimentally determined values, fold increase in 50% protective dose was calculated and is shown in Table 6

TABLE 6

| Fluoroquinolone | Fold Increase |
|---|---|
| Ciprofloxacin | >10 |
| Ofloxacin | 10 |
| Levofloxacin | 8-10 |
| S-(−)-Nadifloxacin | 0 |

Test Example 1

Equilibrium Moisture Content Determination of S-(−)-9-fluoro-6,7-dihydro-8-(4-hydroxypiperidin-1-yl)-5-methyl-1-oxo-1H,5H-benzo[i,j]quinolizine-2-carboxylic acid anhydrate and S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate.

Silica (anhydrous) and three saturated solutions of electrolytes prepared by dissolving the respective salts in water were each introduced into different desiccators to control the inner relative humidity to a specific value as represented in the following Table 7. Then, the equilibrium moisture contents of S-(−)-9-fluoro-6,7-dihydro-8-(4-hydroxypiperidin-1-yl)-5-methyl-1-oxo-1H,5H-benzo[i,j]quinolizine-2-carboxylic acid anhydrate and S-(−)-9-fluoro-6,7-dihydro-8-(4-hydroxypiperidin-1-yl)-5-methyl-1-oxo-1H,5H-benzo[i,j]quinolizine-carboxylic acid 0.2 hydrate prepared in Examples 1 and 2-respectively were determined at several relative humidities.

TABLE 7

| Powder/Saturated salt solutions inside the dessicator. | |
|---|---|
| Powder/Salt Solution | Relative humidity (%) at 27° C. |
| Silica | 20% |
| Ammonium Nitrate | 58% |
| Sodium Chloride | 75% |
| Potassium Nitrate | 95% |

Figure 2:
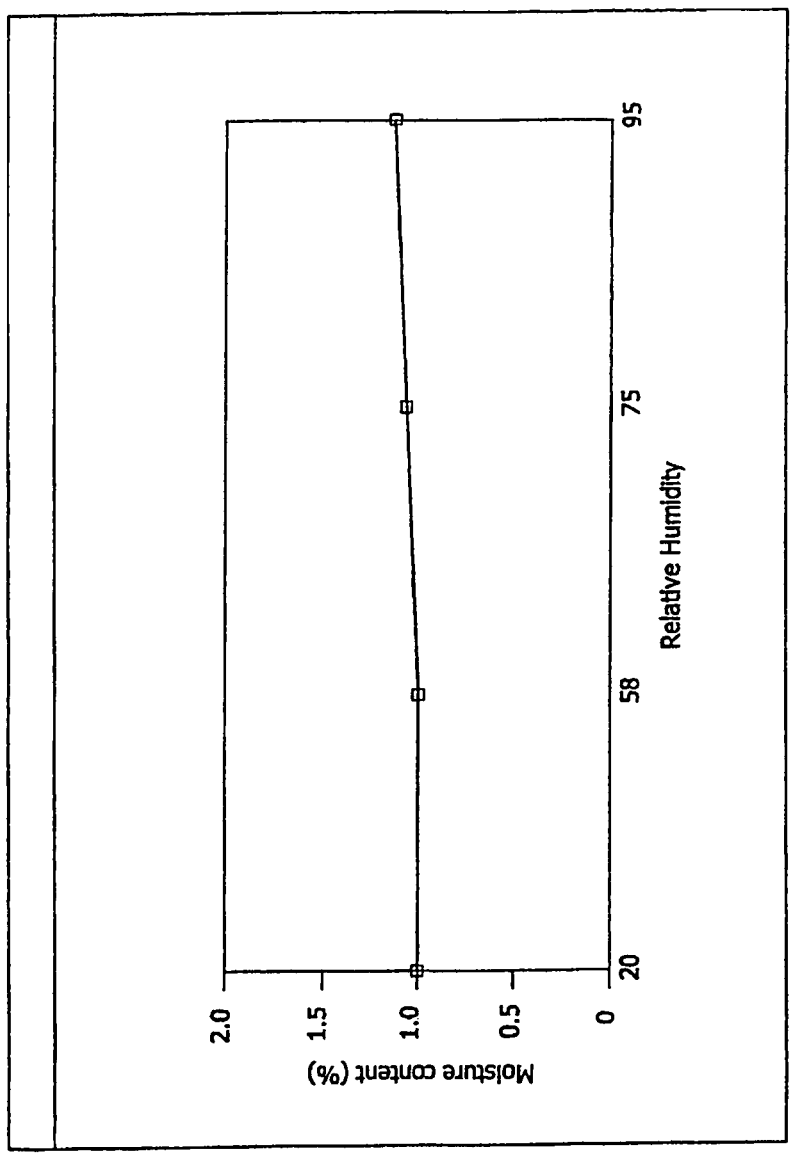
FIG. 2 represents the equilibrium moisture content of S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate at a relative humidity of 20% to 95%.
3.

Specifically, 1 g of the sample was spread on a pre-weighed petridish and the total weight was accurately measured, then both the samples were placed in each desiccator of Table 8 The desiccators were allowed to stand at normal temperature for at least 3 days and the weight was measured agingly over this period. The weight changes were tabulated. At the end of 3 days all samples were taken to be weighed. The moisture content of each sample was determined by Karl Fischer analysis. Equilibrium moisture content at each relative humidity is represented in FIG. 1 (anhydrate) and FIG. 2 (0.2 hydrate). FIG. 2 shows that the moisture content of the 0.2 hydrate is maintained around 1% for the whole humidity range tested (20% to 95%). FIG. 1 shows that the moisture content of the anhydrate is maintained around 0.1% at the relative humidity 20% to 58%. At humidities of about 75% the anhydrate shows weight change and reaches a new equilibrium which is maintained around 1% for the relative humidity range 75% to 95% and corresponds to the 0.2 hydrate (by Karl Fisher measurements and X-ray diffraction analysis). The 0.2 hydrate displays superior stability since it keeps a constant equilibrium moisture content regardless of relative humidity change.

Test Example 2

X-Ray Diffraction Analysis

After 300 mg each of S-(−)-9-fluoro-6,7-dihydro-8-(4-hydroxypiperidin-1-yl)-5-methyl-1-oxo-1H,5H-benzo[i,j] quinolizine-2-carboxylic acid anhydrate (prepared as in Example 1) and S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate (prepared as in Example2) were thinly spread on the sample holder X-ray diffraction analyses (40 kv×40 mA Rigaku D/max 2200) were performed under the conditions listed below:
scan speed (2θ) 5°/min
sampling time 7 min
scan mode: continuous
2θ/θ reflection
Cu target (No filter)
Results of the X-ray diffraction analysis on anhydrate and 0.2 hydrate were as depicted in FIGS. 3 and 4 respectively. From these spectra it can be verified that their crystal forms differ from each other.

Test Example 3

Thermal Analysis of the S-(−)-9-fluoro-6,7-dihydro-8-(4-hydroxypiperidin-1-yl)-5-methyl-1-oxo-1H,5H-benzo[i,j] quinolizine-2-carboxylic acid anhydrate (prepared as in Example 1) and S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate anhydride (prepared as in Example2).

For the Differential Scanning Calorimetry, PERKIN ELMER DSC 7 system was used. 3 mg of the sample was weighed into the aluminum pan, which was then press sealed with an aluminum lid. After three tiny needle holes were made on the lid the sample was tested by heating from (15° C.) to (300° C.) at a rate of 20° C./min. As can be seen from the FIG. 8 there is an endothermic peak which begins at around 150° C., and an exothermic peak due to thermal decomposition at around 240° C. to 264° C. In contrast the anhydrate shows only an exothermic peak at around 245° C. to 268° C. without any endothermic peak.

Test Example 4

Chemical Stability Under Heating

The chemical stability of S-(−)-9-fluoro-6,7-dihydro-8-(4-hydroxypiperidin-1-yl)-5-methyl-1-oxo-1H,5H-benzo[i,j] quinolizine-2-carboxylic acid anhydrate (prepared as in Example 1) and S-(−)-9-fluoro-6,7-dihydro-8-(4-hydroxypiperidin-1-yl)-5-methyl-1-oxo-1H,5H-benzo[i,j]quinolizine-2-carboxylic acid 0.2 hydrate (prepared as in Example 2), S-(−)-9-fluoro-6,7-dihydro-8-(4-hydroxypiperidin-1-yl)-5-methyl-1-oxo-1H,5H-benzo[i,j]quinolizine-2-carboxylic acid 0.5 hydrate (prepared as in Example 3) and S-(−)-9-fluoro-6,7-dihydro-8-(4-hydroxypiperidin-1-yl)-5-methyl-1-oxo-1H,5H-benzo[i,j]quinolizine-2-carboxylic acid 0.75 hydrate (prepared as in Example 4) were compared in order to determine the effect on chemical stability of the extent of hydration.

The anhydride and hydrates were each introduced into a glass vial and maintained at 70° C. Thus the thermal decomposition with elapsed time was analyzed by HPLC and the results thus obtained are described in Table 8

TABLE 8

Thermal stability with elapsed time at 70° C. (Unit %)

| Sample | Initial | Time (week) 1 | 2 |
| --- | --- | --- | --- |
| Anhydrate | 98.9 | 98.7 | 98.6 |
| 0.2 hydrate | 98.7 | 98.0 | 98.1 |
| 0.5 hydrate | 98.1 | 97.0 | 96.1 |
| 0.75 hydrate | 98.3 | 97.1 | 97.2 |

As can be seen the 0.2 hydrates shows the same degree of chemical stability as the anhydrate, whilst the 0.5 hydrate and 0.75 hydrate decompose with time.

Test Example 5

Water Solubility of S-(−)-9-fluoro-6,7-dihydro-8-(4-hydroxypiperidin-1-yl)-5-methyl-1-oxo-1H,5H-benzo[i,j] quinolizine-2-carboxylic acid anhydrate (prepared as in Example 1), S-(−)-9-Fluoro-6,7-dihydro-8-(4-hydroxypiperidin-1-yl)-5-methyl-1-oxo-1H,5H-benzo[i,j]quinolizine-2-carboxylic acid 0.2 hydrate (prepared as in Example 2), S-(−)-9-fluoro-6,7-dihydro-8-(4-hydroxypiperidin-1-yl)-5-methyl-1-oxo-1H,5H-benzo[i,j]quinolizine-2-carboxylic acid sodium salt monohydrate (prepared as in Example 5), S-(−)-9-fluoro-6,7-dihydro-8-(4-hydroxypiperidin-1-yl)-5-methyl-1-oxo-1H,5H-benzo[i,j]quinolizine-2-carboxylic acid arginine salt 0.75 hydrate (prepared as in Example 8), 8-{4[2(R)-amino-3-phenylpropionyloxy]piperidin-1-yl}-9-fluoro-5(S)-methyl-6,7dihydro-1-oxo-1H,5H-benzo[i,j]quinolizine-2-carboxylic acid acetate(prepared as in Example 30).

Water solubilities of the compounds listed above were measured. The measurement results are listed in Table 9

TABLE 9

Water Solubility at 27° C.

| Sample | Distilled Water (pH 6.8) |
| --- | --- |
| Anhydrate | 0.19 mg/ml |
| 0.2 hydrate | 0.24 mg/ml |
| Na Salt.H$_2$O | >1000 mg/ml |
| Arginine Salt.0.25H$_2$O | 75 mg/ml |
| Arginine Salt.0.75H$_2$O | 94 mg/ml |
| D-Ala-S-(Nadifloxacin).AcOH | >250 mg/ml |

As can be seen from the above results, the salt shows superior water solubility.

The following examples relate to S-(−)-9-fluoro-8(4-hydroxypiperidin-1-yl)-5-methyl-6,7-dihydro-1-oxo-1H,5H-benzo[i,j]quinolizine-2-carboxylic acid, its salts, prodrugs, derivatives and hydrates thereof of the Formula I, wherein the percentages indicated in the examples for the salts, prodrugs, derivatives and hydrate of the compounds of the invention are calculated on the basis of S-(−)-9-fluoro-8(4-hydroxypiperidin-1-yl)-5-methyl-6,7-dihydro-1-oxo-1H,5H-benzo[i,j] quinolizine-2-carboxylic acid.

Composition Example 1

| Tablet composition | |
| --- | --- |
| Ingredient | % w/w |
| 1. S-(−)-9-fluoro-8(4-hydroxypiperidin-1-yl)-5-methyl-6,7-dihydro-1-oxo-1H,5H-benzo[i,j]quinolizine-2-carboxylic acid or an optically pure compound of the invention of formula I. | 10-90 |
| 2. Cyclodextrin & derivatives | 5-40 |
| 3. Sodium citrate | 0.1-5 |
| 4. Microcrystalline cellulose | 1-50 |
| 5. Polyvinyl pyrrolidone | 0.1-9 |
| 6. Cross carmellose sodium | 0.1-5 |
| 7. Starch | 2-30 |
| 8. Lactose | 2-40 |
| 9. Magnesium stearate | 0.1-5 |
| 10. Talc purified | 0.1-5 |
| 11. Hydroxypropyl methyl cellulose | 0.1-6 |
| 12. Polyethylene glycol 400 | 0.1-2 |
| 13. Titanium Dioxide | 0.1-2 |

The active ingredient S-(−)-9-fluoro-8(4-hydroxypiperidin-1-yl)-5-methyl-6,7-dihydro-1-oxo-1H,5H-benzo[i,j] quinolizine-2-carboxylic acid or an optically pure compound of the invention of formula I is mixed with cyclodextrin and its derivatives, sodium citrate, microcrystalline cellulose, corn starch and lactose. Wet granulate with polyvinyl pyrrolidone. Dry the granulate. Mix with cross carmellose sodium, magnesium stearate and talc purified. Compress the tablets.

Film coat the tablets using mixture of hydroxypropylmethyl cellulose, polyethylene glycol 400 and titanium dioxide in appropriate solvent.

Composition Example 2

Injection Composition

| Ingredient | % w/v |
|---|---|
| 1. S-(−)-9-fluoro-8(4-hydroxypiperidin-1-yl)-5-methyl-6,7-dihydro-1-oxo-1H,5H-benzo[i,j]quinolizine-2-carboxylic acid or an optically pure compound of the invention of formula I. | Up to 10 |
| 2. Sodium citrate | 0-3 |
| 3. Sodium hydroxide q.s. and trometamol q.s. to adjust pH between 8.0-9.9 | q.s. |
| 4. Disodium edetate | 0-0.5 |
| 5. Water for injection | q.s. to 100 |

The active ingredient S-(−)-9-fluoro-8(4-hydroxypiperidin-1-yl)-5-methyl-6,7-dihydro-1-oxo-1H,5H-benzo[i,j]quinolizine-2-carboxylic acid or an optically pure compound of the invention of formula I and sodium citrate is dissolved in water for injection. Disodium edetate is added and dissolved. pH is adjusted with 1% sodium hydroxide solution and trometamol. Volume to be made. Filter through 0.2 micron membrane filter. Fill in vials and autoclave at 121° C. for 15 minutes.

Composition Example 3

Injection Formulation

| Ingredient | % w/v |
|---|---|
| 1. S-(−)-9-fluoro-8(4-hydroxypiperidin-1-yl)-5-methyl-6,7-dihydro-1-oxo-1H,5H-benzo [i,j]quinolizine-2-carboxylic acid or an optically pure compound of the invention of fomula I. | Up to 10 |
| 2. L-arginine | 0.1-10 |
| 3. Sodium citrate | 0-3.5 |
| 4. Sodium hydroxide to adjust pH between 8.0-9.9 | q.s. |
| 5. Disodium edetate | 0-0.5 |
| 6. Water for injection | q.s. to 100 |

Dissolve L-arginine in water for injection. Add and dissolve S-(−)-9-fluoro-8(4-hydroxypiperidin-1-yl)-5-methyl-6,7-dihydro-1-oxo-1H,5H-benzo[i,j]quinolizine-2-carboxylic acid or an optically pure compound of the invention of formula I by stirring in above solution. Add sodium citrate and dissolve. Add disodium edetate and dissolve by stirring. Check pH and adjust if necessary with 1% sodium hydroxide solution. Make up volume with water for injection. Sterilize by filtration through 0.2μ membranes. Fill in to containers aseptically and seal.

Composition Example 4

Topical Composition

A typical pharmaceutical cream containing 1% S-(−)-9-fluoro-8(4-hydroxypiperidin-1-yl)-5-methyl-6,7-dihydro-1-oxo-1H,5H-benzo[i,j]quinolizine-2-carboxylic acid or an optically pure compound of the invention of formula I was prepared using the following composition:

| Ingredient | % w/v |
|---|---|
| S-(−)-9-fluoro-8(4-hydroxypiperidin-1-yl)-5-methyl-6,7-dihydro-1-oxo-1H,5H-benzo[i,j] quinolizine-2-carboxylic acid or an optically pure compound of the invention of formula I | 0.1-10 |
| Diethanolamine | 0.1-2 |
| Trometamol | 0-0.5 |
| Sodium hydroxide q.s. to adjust pH between 8.0-9.9 | q.s. |
| Liquid paraffin | 0-20 |
| Microcrystalline wax | 0-10 |
| Cetomacrogol 1000 | 0.1-5 |
| Propylene glycol | 0-20 |
| Disodium EDTA | 0-0.5 |
| Sodium disulphite | 0-0.5 |
| Cetostearyl alcohol | 0.1-15 |
| Purified water | q.s. to 100 |

The active ingredient is S-(−)-9-fluoro-8(4-hydroxypiperidin-1-yl)-5-methyl-6,7-dihydro-1-oxo-1H,5H-benzo[i,j]quinolizine-2-carboxylic acid or an optically pure compound of the invention of formula I. The remaining components are inert or auxiliary. The composition of liquid paraffin, microcrystalline wax and cetomacrogol 1000 is prepared and added to the solution of S-(−)-9-fluoro-8(4-hydroxypiperidin-1-yl)-5-methyl-6,7-dihydro-1-oxo-1H,5H-benzo[i,j]quinolizine-2-carboxylic acid or an optically pure compound of the invention of formula I in a mixture of diethanolamine/trometamol. The mixture is homogenized and to the resultant cream is added propylene glycol, sodium bisulphite and disodium EDTA. The composition is made up to 100% with purified water to give the final composition. The cream is stable when stored at a temperature not exceeding 35° C. The pH of stability is between 8.0 to 9.5.

What is claimed is:

1. A compound: S-(−)-9-fluoro-6,7-dihydro-8-(4-hydroxypiperidin-1-yl)-5-methyl-1-oxo-1H,5H-benzo[i,j]quinolizine-2-carboxylic acid lysine salt.

2. An injectable pharmaceutical composition comprising S-(−)-9-fluoro-6,7-dihydro-8-(4-hydroxypiperidin-1-yl)-5-methyl-1-oxo-1H,5H-benzo[i,j]quinolizine-2-carboxylic acid lysine salt and one or more pharmaceutically acceptable excipients.

3. The pharmaceutical composition of claim 2, for systemic use.

4. The pharmaceutical composition of claim 2, wherein the composition is administered by intravenous, intramuscular or subcutaneous route.

5. The pharmaceutical composition of claim 2, wherein the one or more pharmaceutically acceptable excipients is an agent which facilitates aqueous solubility of S-(−)-9-fluoro-6,7-dihydro-8-(4-hydroxypiperidin-1-yl)-5-methyl-1-oxo-1H,5H-benzo[i,j]quinolizine-2-carboxylic acid lysine salt.

* * * * *